US011653831B2

(12) United States Patent
Hakoshima

(10) Patent No.: US 11,653,831 B2
(45) Date of Patent: May 23, 2023

(54) VISUAL PERFORMANCE EXAMINATION DEVICE, VISUAL PERFORMANCE EXAMINATION METHOD, AND COMPUTER PROGRAM

(71) Applicant: JVC KENWOOD Corporation, Yokohama (JP)

(72) Inventor: Shuji Hakoshima, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 148 days.

(21) Appl. No.: 17/242,384

(22) Filed: Apr. 28, 2021

(65) Prior Publication Data

US 2021/0244270 A1  Aug. 12, 2021

Related U.S. Application Data

(63) Continuation of application No. 16/409,968, filed on May 13, 2019, now Pat. No. 11,019,994, which is a continuation of application No. PCT/JP2017/039791, filed on Nov. 2, 2017.

(30) Foreign Application Priority Data

Dec. 28, 2016 (JP) .............................. JP2016-256645
Dec. 28, 2016 (JP) .............................. JP2016-256646

(51) Int. Cl.
*A61B 3/11* (2006.01)
*A61B 3/00* (2006.01)
(Continued)

(52) U.S. Cl.
CPC ............ *A61B 3/111* (2013.01); *A61B 3/0008* (2013.01); *A61B 3/032* (2013.01); *A61B 3/085* (2013.01);
(Continued)

(58) Field of Classification Search
CPC ....... A61B 3/111; A61B 3/0008; A61B 3/032; A61B 3/085; A61B 3/10; A61B 3/113; A61B 3/14; A61B 3/0083; A61B 3/152
(Continued)

(56) References Cited

U.S. PATENT DOCUMENTS 10,379,610 B2 * 8/2019 Yasuda .................... G06F 3/013
2009/0257024 A1 * 10/2009 Luther ...................... A61B 3/14
351/221
(Continued)

FOREIGN PATENT DOCUMENTS

JP  2014-530730  11/2014
JP  2015-525597  9/2015

OTHER PUBLICATIONS

U.S. Appl. No. 16/409,968, filed May 13, 2019.
(Continued)

*Primary Examiner* — Mohammed A Hasan
(74) *Attorney, Agent, or Firm* — Amin, Turocy & Watson, LLP

(57) ABSTRACT

A visual performance examination device includes a display control unit that displays an indicator at each of a plurality of positions in a display screen of a display device; an image data obtaining unit that obtains an image data of eyes of a test subject, which are irradiated with a detection light emitted from a light source; a position calculating unit that, based on the image data, calculates a position data of corneal reflexes of the eyes when each of a plurality of indicators displayed at the positions in the display screen is shown; and an evaluating unit that, based on relative positions of the indicators and relative positions of the corneal reflexes, outputs evaluation data about visual performance of the test subject.

6 Claims, 31 Drawing Sheets

(51) Int. Cl.
*A61B 3/032* (2006.01)
*A61B 3/08* (2006.01)
*A61B 3/14* (2006.01)
*A61B 3/10* (2006.01)
*A61B 3/113* (2006.01)

(52) U.S. Cl.
CPC ............... *A61B 3/10* (2013.01); *A61B 3/113* (2013.01); *A61B 3/14* (2013.01)

(58) Field of Classification Search
USPC ........................................................ 351/204
See application file for complete search history.

(56) References Cited

U.S. PATENT DOCUMENTS

| | | | | |
|---|---|---|---|---|
| 2013/0109955 | A1* | 5/2013 | Assmann | A61B 5/055 600/411 |
| 2014/0268051 | A1 | 9/2014 | Maor et al. | |
| 2014/0285768 | A1 | 9/2014 | Barnard et al. | |
| 2015/0265146 | A1 | 9/2015 | Bloom et al. | |
| 2018/0322953 | A1* | 11/2018 | Schmidt | G16H 50/70 |
| 2018/0356882 | A1* | 12/2018 | Kaneko | G06F 3/012 |

OTHER PUBLICATIONS

International Search Report and Written Opinion for International Patent Application No. PCT/JP2017/039791 dated Feb. 6, 2018, 9 pages.

\* cited by examiner

VISUAL PERFORMANCE EXAMINATION DEVICE, VISUAL PERFORMANCE EXAMINATION METHOD, AND COMPUTER PROGRAM

CROSS-REFERENCE TO RELATED APPLICATION(S)

This application is a Continuation of application Ser. No. 16/409,968, filed on May 13, 2019, which is a Continuation of PCT international application Ser. No. PCT/JP2017/039791 filed on Nov. 2, 2017 which designates the United States, incorporated herein by reference, and which claims the benefit of priority from Japanese Patent Application No. 2016-256645, filed on Dec. 28, 2016 and Japanese Patent Application No. 2016-256646 filed on Dec. 28, 2016, incorporated herein by reference.

BACKGROUND

1. Technical Field

The present disclosure relates to a visual performance examination device, a visual performance examination method, and a computer program.

2. Description of the Related Art

At the time of performing visual performance examination such as ocular alignment examination or refraction test, a visual performance examination device is used. A visual performance examination device is meant for examining the abnormality in the visual performance, such as strabismus or amblyopia. As an example of ocular alignment examination, the Hirschberg method is known in which the test subject is irradiated with infrared light emitted from a light source; the eyes of the test subject that are irradiated with infrared light are captured using a camera; the positions of the corneal reflexes that represent the reflected images of the light source on the corneal surfaces are detected; and the ocular alignment of the test subject is examined. Patent Literature 1: Japanese National Publication of International Patent Application No. 2015-525597 A is known.

In the case of performing ocular alignment examination based on the Hirschberg method, in case there is variation in the relative position between the light source and the test subject, there is a possibility that the examination accuracy undergoes a decline. In order to hold down the variation in the relative position between the light source and the test subject; for example, the head portion of the test subject needs to be keep fixed. In that regard, there is a demand for a technology by which, even if there is variation in the relative position between the light source and the test subject, it becomes possible to hold down a decline in the examination accuracy.

SUMMARY

It is an object of the present disclosure to at least partially solve the problems in the conventional technology.

According to an aspect of the present disclosure, a visual performance examination device includes an image data obtaining unit that obtains image data of right eye and image data of left eye of a test subject who is irradiated with a detection light emitted from a light source, a position calculating unit that based on the image data of the right eye, calculates first-type relative position data indicating relative position between pupil and corneal reflex of the right eye, and based on the image data of the left eye, calculates second-type relative position data indicating relative position between pupil and corneal reflex of the left eye, and an evaluating unit that, based on the first-type relative position data and the second-type relative position data, outputs evaluation data about visual performance of the test subject. The first-type relative position data contains time-series data of relative positions between the pupil and the corneal reflex of the right eye in a specified time period, the second-type relative position data contains time-series data of relative positions between the pupil and the corneal reflex of the left eye in the specified time period, and the evaluating unit outputs the evaluation data based on variation in the relative positions between the pupil and the corneal reflex of the right eye in the specified time period, and variation in the relative positions between the pupil and the corneal reflex of the left eye in the specified time period. Based on the first-type relative position data and the second-type relative position data in the specified time period, the position calculating unit calculates time-series data of distances D between corneal reflex of the right eye and corneal reflex of the left eye when position of the pupil of the right eye and position of the pupil of the left eye are set to be coincident in a predetermined plane, and the evaluating unit outputs the evaluation data based on representative value of the distances D within the specified time period.

DETAILED DESCRIPTION OF THE PREFERRED EMBODIMENTS

Exemplary embodiments of the present disclosure are described below with reference to the accompanying drawings. However, the present disclosure is not limited by the embodiments. Moreover, the constituent elements according to the embodiments described below can be combined in an appropriate manner. Furthermore, there are times when some of the constituent elements are not used.

In the following explanation, the positional relationships among the constituent elements are explained by setting a three-dimensional global coordinate system. Herein, the direction parallel to the X-axis in a predetermined plane is treated as the X-axis direction, the direction parallel to the Y-axis that is orthogonal to the X-axis in the predetermined plane is treated as the Y-axis direction, and the direction parallel to the Z-axis that is orthogonal to each of the X-axis and the Y-axis is treated as the Z-axis direction. The predetermined plane includes the X-Y plane.

First Embodiment

Figure 1:
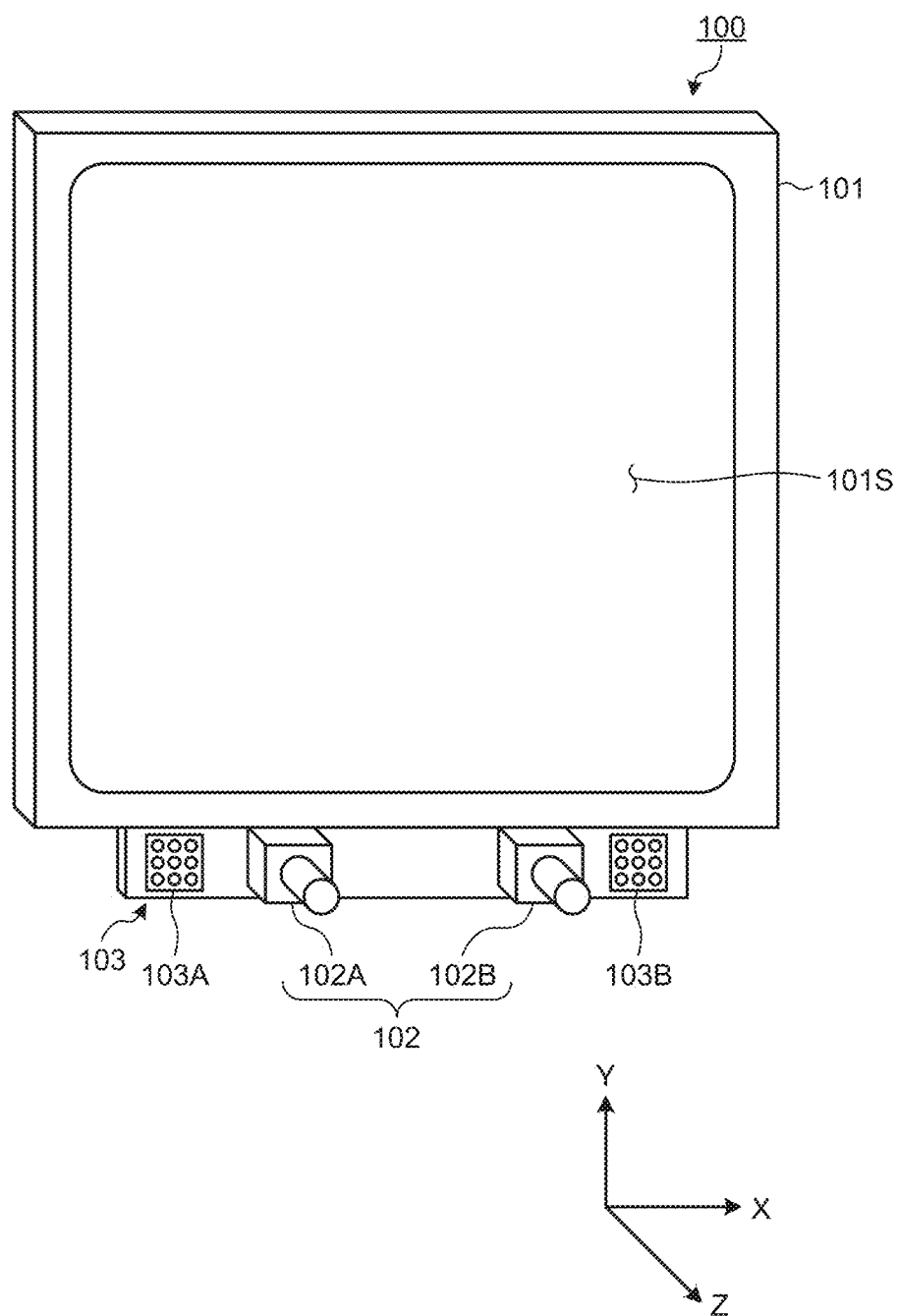
FIG. 1 is a perspective view that schematically illustrates an example of a visual performance examination device according to a first embodiment.

Given below is the explanation of a first embodiment. FIG. 1 is a perspective view that schematically illustrates an example of a visual performance examination device 100 according to the first embodiment. The visual performance examination device 100 is used to examine the abnormality in the visual performance of test subjects. The abnormality in the visual performance includes strabismus or amblyopia. The following explanation is given about an example in which the visual performance examination device 100 is used to examine strabismus of the test subject.

[Brief Overview of Visual Performance Examination Device]

As illustrated in FIG. 1, the visual performance examination device 100 includes a display device 101, a stereo camera device 102, and a light source 103.

The display device 101 includes a flat panel display such as a liquid crystal display (LCD) or an organic electroluminescence display (OLED).

In the first embodiment, a display screen 101S of the display device 101 is essentially parallel to the X-Y plane. The X-axis direction represents the horizontal direction of the display screen 101S, the Y-axis direction represents the vertical direction of the display screen 101S, and the Z-axis direction represents the depth direction that is orthogonal to the display screen 101S.

The stereo camera device 102 takes images of a test subject and obtains image data of the test subject. The stereo camera device 102 includes a first camera 102A and a second camera 102B that are disposed at different positions. Moreover, the stereo camera device 102 is disposed below the display screen 101S of the display device 101. The first camera 102A and the second camera 102B are disposed along the X-axis direction. The first camera 102A is disposed more in the −X direction than the second camera 102B. The first camera 102A as well as the second camera 102B each includes an infrared camera; and includes an optical system capable of transmitting near-infrared rays having the wavelength of, for example, 850 [nm], and includes an imaging element capable of receiving near-infrared rays.

The light source 103 emits a detection light. Moreover, the light source 103 includes a first light source 103A and a second light source 103B that are disposed at different positions. Furthermore, the light source 103 is disposed below the display screen 101S of the display device 101. The first light source 103A and the second light source 103B are disposed along the X-axis direction. The first light source 103A is disposed more in the −X direction than the first camera 102A, while the second light source 103B is disposed more in the +X direction than the second camera 102B. The first light source 103A as well as the second light source 103B each includes an LED (light emitting diode) light source and is capable of emitting near-infrared rays having the wavelength of, for example, 850 [nm]. Meanwhile, the first light source 103A and the second light source 103B may be disposed in between the first camera 102A and the second camera 102B.

Figure 2:
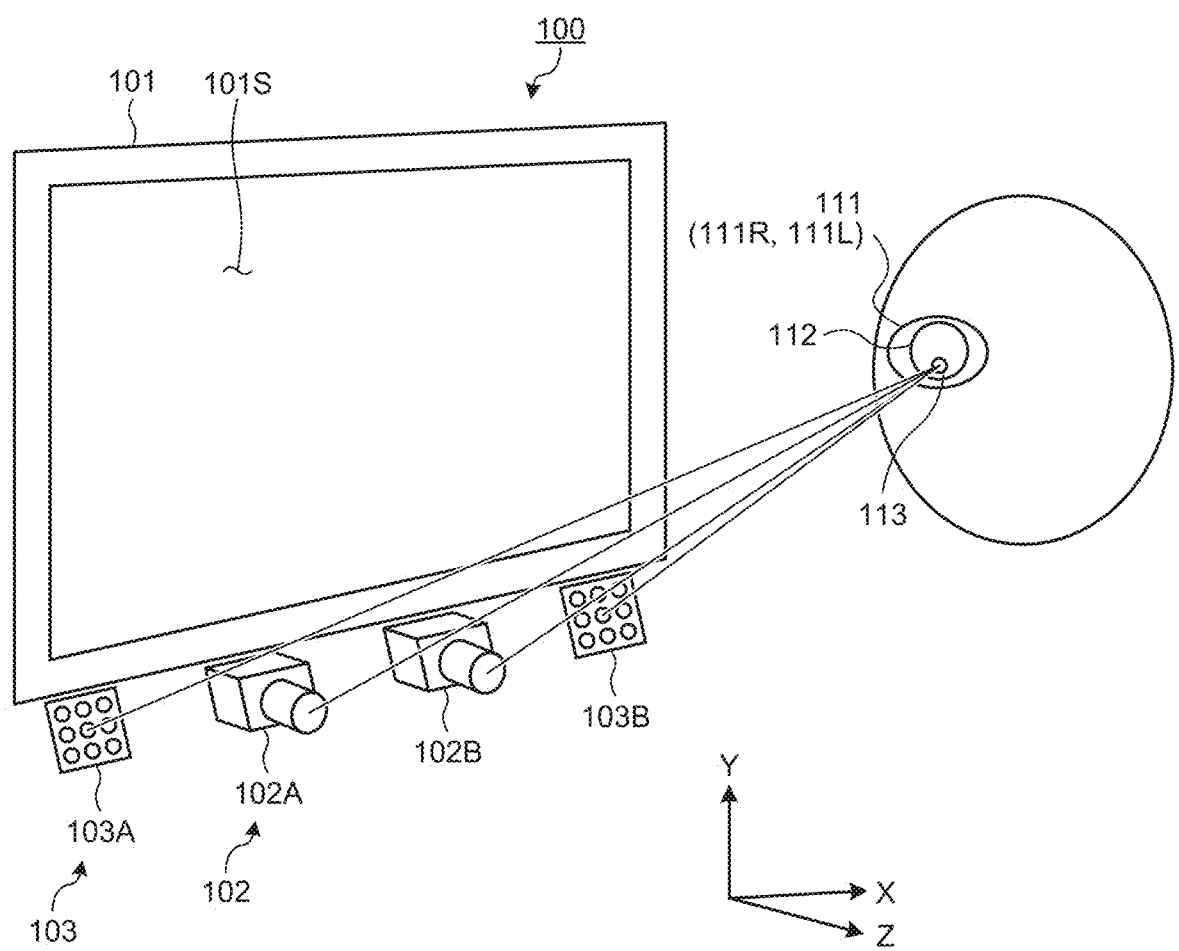
FIG. 2 is a diagram that schematically illustrates the positional relationships among a display device, a stereo camera device, a light source, and the eyes of a test subject according to the first embodiment.

FIG. 2 is a diagram that schematically illustrates the positional relationships among the display device 101, the stereo camera device 102, the light source 103, and eyes 111 of the test subject according to the first embodiment. The eyes 111 of the test subject include a right eye 111R and a left eye 111L of the test subject.

The light source 103 emits infrared light representing the detection light and lights up the eyes 111 of the test subject. When the eyes 111 are irradiated with the detection light emitted from the first light source 103A, the stereo camera device 102 takes images of the eyes 111 using the second camera 102B. Similarly, when the eyes 111 are irradiated with the detection light emitted from the second light source 103B, the stereo camera device 102 takes images of the eyes 111 using the first camera 102A.

From at least either the first camera 102A or the second camera 102B, a frame synchronization signal is output. The first light source 103A and the second light source 103B emit the detection light based on the frame synchronization signal. When the detection light emitted from the second light source 103B falls on the eyes 111, the first camera 102A obtains the image data of the eyes 111. When the detection light emitted from the first light source 103A falls on the eyes 111, the second camera 102B obtains the image data of the eyes 111.

When the detection light falls on the eyes 111, some part of the detection light gets reflected from pupils 112. The light reflected from the pupils 112 enters the stereo camera device 102. Moreover, when the detection light falls on the eyes 111, corneal reflexes 113 is formed in the eyes 111. The corneal reflexes 113 represent reflected images of the light source 103 on the corneal surfaces. The light coming from the corneal reflexes 113 enters the stereo camera device 102.

When the relative position of the first camera 102A and the second camera 102B with respect to the first light source 103A and the second light source 103B is appropriately set, the light entering the stereo camera device 102 from the pupils 112 becomes weaker in intensity and the light entering the stereo camera device 102 from the corneal reflexes 113 becomes stronger in intensity. That is, in the stereo camera device 102, the obtained images of the pupils 112 become low-brightness images, and the obtained images of the corneal reflexes 113 become high-brightness images. Based on the brightness of the obtained images, the stereo camera device 102 becomes able to detect the positions of the pupils 112 and the positions of the corneal reflexes 113.

[Hardware Configuration]

Figure 3:
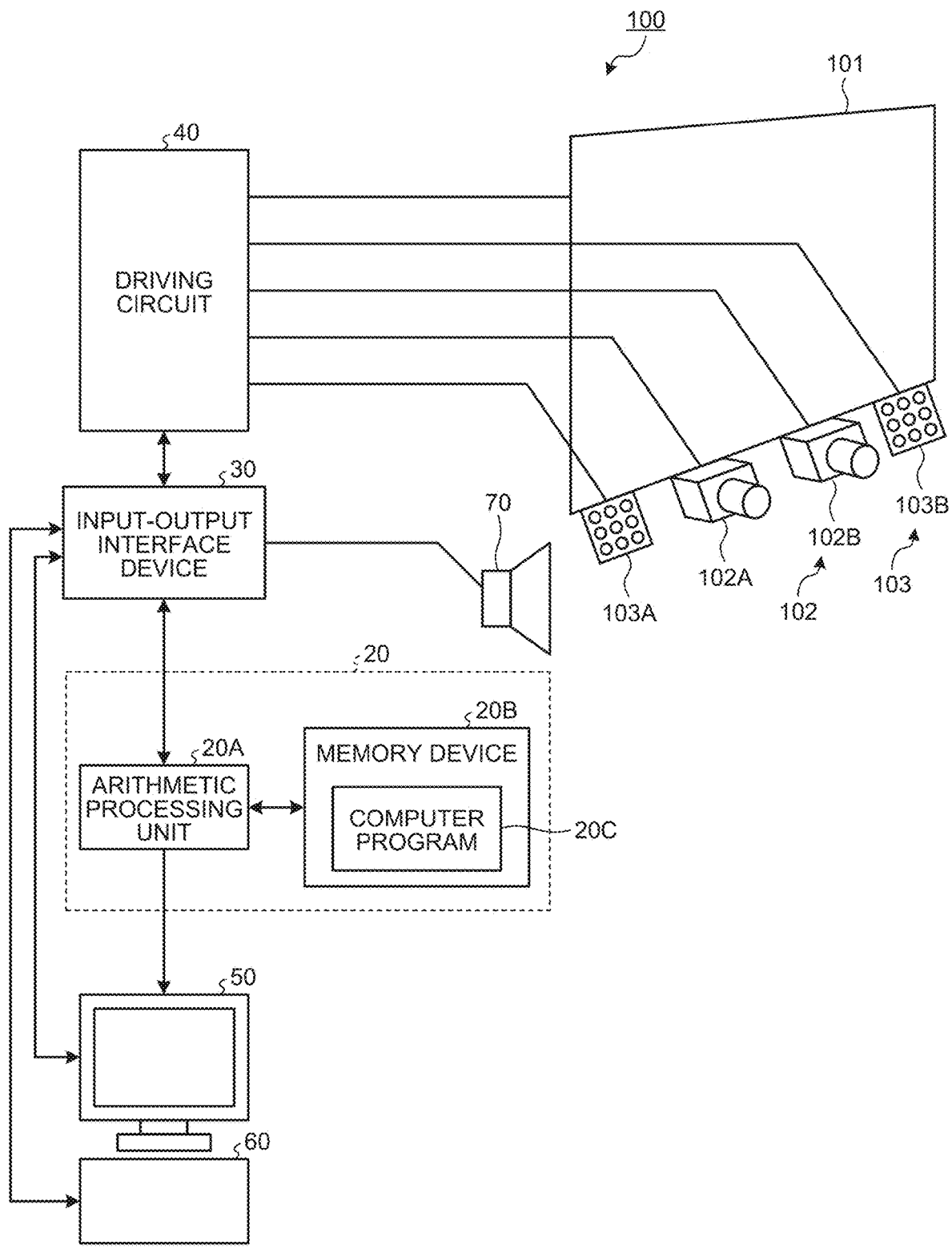
FIG. 3 is a diagram illustrating an exemplary hardware configuration of the visual performance examination device according to the first embodiment.

FIG. 3 is a diagram illustrating an exemplary hardware configuration of the visual performance examination device 100 according to the first embodiment. As illustrated in FIG. 3, the visual performance examination device 100 includes the display device 101, the stereo camera device 102, the light source 103, a computer system 20, an input-output interface device 30, a driving circuit 40, an output device 50, an input device 60, and an audio output device 70. The computer system 20 includes an arithmetic processing unit 20A and a memory device 20B. The memory device 20B is used to store a computer program 20C.

The computer system 20, the driving circuit 40, the output device 50, the input device 60, and the audio output device 70 perform data communication via the input-output interface device 30.

The arithmetic processing unit 20A includes a microprocessor such as a CPU (central processing unit). The memory device 20B includes a nonvolatile memory such as a ROM (read only memory) or a volatile memory such as a RAM (random access memory). The arithmetic processing unit 20A performs arithmetic processing according to the computer program 20C that is stored in the memory device 20B.

The driving circuit 40 generates driving signals and outputs them to the display device 101, the stereo camera device 102, and the light source 103. Moreover, the driving circuit 40 provides the image data of the eyes 111, which is obtained by the stereo camera device 102, to the computer system 20 via the input-output interface device 30.

The output device 50 includes a display device such as a flat panel display. Moreover, the output device 50 may also include a printing device. The input device 60 generates input data as a result of getting operated. Moreover, the input device 60 includes a keyboard or a mouse to be used in a computer system. Meanwhile, the input device 60 may also include a touch-sensitive panel disposed on the display screen of the output device 50 that functioning as the display device. The audio output device 70 includes a speaker and, for example, outputs an audio for calling attention to the test subject.

In the first embodiment, the display device 101 and the computer system 20 are configured as different devices. However, alternatively, the display device 101 and the computer system 20 can be configured as an integrated device. For example, when the visual performance examination device 100 includes a tablet personal computer; the computer system 20, the input-output interface device 30, the driving circuit 40, and the display device 101 may be installed in the tablet personal computer.

Figure 4:
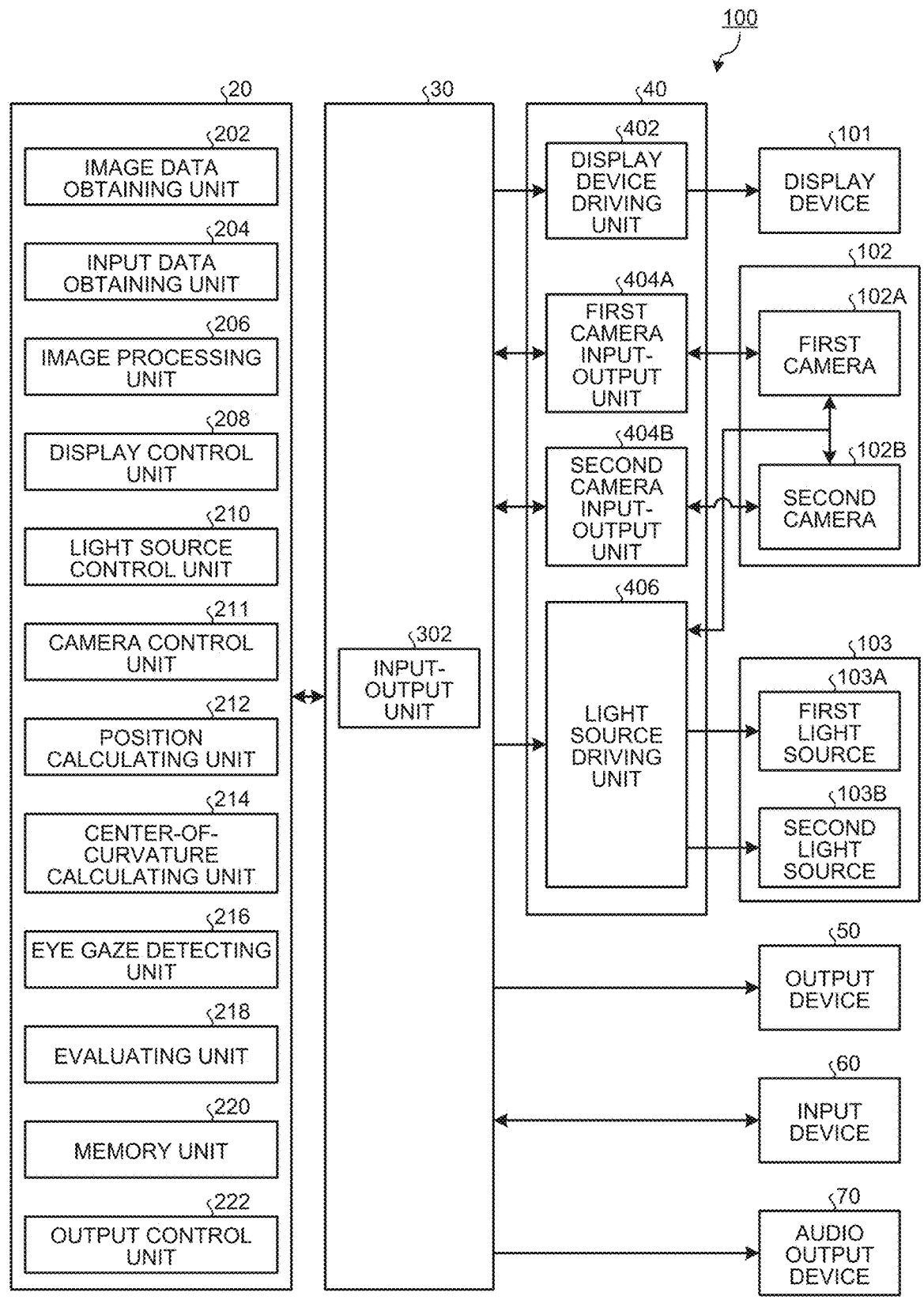
FIG. 4 is a functional block diagram illustrating an example of the visual performance examination device according to the first embodiment.

FIG. 4 is a functional block diagram illustrating an example of the visual performance examination device 100 according to the first embodiment. As illustrated in FIG. 4, the input-output interface device 30 includes an input-output unit 302. The driving circuit 40 includes a display device driving unit 402 that generates driving signals meant for driving the display device 101, and outputs the driving signals to the display device 101; a first camera input-output unit 404A that generates driving signals meant for driving the first camera 102A, and outputs the driving signals to the first camera 102A; a second camera input-output unit 404B that generates driving signals meant for driving the second camera 102B, and outputs the driving signals to the second camera 102B; and a light source driving unit 406 that generates driving signals meant for driving the first light source 103A and the second light source 103B, and outputs the driving signals to the first light source 103A and the second light source 103B. Moreover, the first camera input-output unit 404A provides the image data of the eyes 111, which is obtained by the first camera 102A, to the computer system 20 via the input-output unit 302. Similarly, the second camera input-output unit 404B provides the image data of the eyes 111, which is obtained by the second camera 102B, to the computer system 20 via the input-output unit 302.

The computer system 20 controls the visual performance examination device 100. The computer system 20 includes an image data obtaining unit 202, an input data obtaining unit 204, an image processing unit 206, a display control unit 208, a light source control unit 210, a camera control unit 211, a position calculating unit 212, a center-of-curvature calculating unit 214, an eye gaze detecting unit 216, an evaluating unit 218, a memory unit 220, and an output control unit 222. These functions of the computer system 20 are implemented due to the arithmetic processing unit 20A, the memory device 20B, and the computer program 20C stored in the memory device 20B.

The image data obtaining unit 202 obtains, from the stereo camera device 102 via the input-output unit 302, the image data of the test subject as obtained by the stereo camera device 102 that includes the first camera 102A and the second camera 102B. Herein, the image data represents digital data. The image data of the test subject includes the image data of the eyes 111 of the test subject. Moreover, the image data of the eyes 111 of the test subject contains the image data of the right eye 111R of the test subject and contains the image data of the left eye 111L of the test subject. The stereo camera device 102 takes images of the eyes 111 of the test subject that are irradiated with the detection light emitted from the light source 103. The image data obtaining unit 202 obtains the image data of the eyes 111 of the test subject, which are irradiated with the detection light emitted from the light source 103, from the stereo camera device 102 via the input-output unit 302.

The input data obtaining unit 204 obtains input data, which is generated when the input device 60 is operated, from the input device 60 via the input-output unit 302.

The image processing unit 206 performs image processing on the image data obtained by the image data obtaining unit 202.

The display control unit 208 displays particular display data in the display device 101. In the first embodiment, the display control unit 208 displays, as display data in the display device 101, an indicator 130 on which the test subject is to be made to fix the eyes. The indicator 130 can be a light spot or can be an illustration. The display control unit 208 can display, in the display device 101, the indicator 130 that remains stationary as well as moves around within the display screen 101S of the display device 101. Alternatively, the display control unit 208 can display the indicators 130 at each of a plurality of positions in the display screen 101S of the display device 101.

The light source control unit 210 controls the light source driving unit 406 for controlling the operating condition of the first light source 103A and the second light source 103B. The light source control unit 210 controls the first light source 103A and the second light source 103B in such a way that the first light source 103A and the second light source 103B emit the detection light at different timings. Moreover, the light source control unit 210 controls the amount of the detection light emitted from the first light source 103A and controls the amount of the detection light emitted from the second light source 103B.

The camera control unit 211 controls the first camera input-output unit 404A and the second camera input-output unit 404B for controlling the operating condition of the stereo camera device 102 that includes the first camera 102A and the second camera 102B.

The position calculating unit 212 calculates position data of the pupils 112 based on the image data of the eyes 111 as obtained by the image data obtaining unit 202. Moreover, the position calculating unit 212 calculates position data of the corneal reflexes 113 based on the image data of the eyes 111 as obtained by the image data obtaining unit 202. Herein, the position calculating unit 212 calculates the position data of the pupils 112 and the position data of the corneal reflexes 113 based on the image data of the eyes 111 that is obtained when the indicator 130 displayed in the display device 101 is shown to the test subject.

Herein, regarding each of the right eye 111R as well as the left eye 111L of the test subject, the position calculating unit 212 calculates the position data of the corresponding pupil 112 and the position data of the corresponding corneal reflex 113. Moreover, based on the image data of the right eye 111R, the position calculating unit 212 calculates first-type relative position data that indicates the relative position between a pupil 112R of the right eye 111R and a corneal reflex 113R of the right eye 111R. Similarly, based on the image data of the left eye 111L, the position calculating unit 212 calculates second-type relative position data that indicates the relative position between a pupil 112L of the left eye 111L and a corneal reflex 113L of the left eye 111L.

In the first embodiment, the position calculating unit 212 calculates, as the position data of each pupil 112, position data of a pupil center 112C present in the X-Y plane. Moreover, the position calculating unit 212 calculates, as the position data of each corneal reflex 113, position data of a corneal reflex center 113C present in the X-Y plane. Each pupil center 112C represents the center of the corresponding pupil 112. Each corneal reflex center 113C represents the center of the corresponding corneal reflex 113.

The center-of-curvature calculating unit 214 calculates position data of a corneal curvature center 110 of each eye 111 based on the image data of that eye 111 as obtained by the image data obtaining unit 202.

The eye gaze detecting unit 216 detects, based on the image data of the eyes 111 as obtained by the image data obtaining unit 202, the eye gaze of the test subject. The eye gaze of the test subject includes an eye gaze vector indicating the eye gaze direction of the test subject. The eye gaze detecting unit 216 detects the eye gaze of the test subject based on the image data of the eyes 111 that is obtained when the indicator 130 displayed in the display device 101 is shown to the test subject. Moreover, based on the position data of the pupil centers 112C and the position data of the corneal curvature centers 110 obtained from the image data of the eyes 111, the eye gaze detecting unit 216 detects each of the eye gaze vector of the right eye 111R and the eye gaze vector of the left eye 111L of the test subject.

Furthermore, based on the detected eye gaze vectors, the eye gaze detecting unit 216 detects position data of the point of regard of the test subject. In the first embodiment, the point of regard of the test subject includes the point of intersection of the eye gaze vectors of the test subject with the display screen 101S of the display device 101. In the first embodiment, the position data of the point of regard implies the position data of the point of intersection of the eye gaze vectors of the test subject with the display screen 101S of the display device 101 in the global coordinate system.

The evaluating unit 218 outputs, based on the position data calculated by the position calculating unit 212, evaluation data about the visual performance of the test subject. The evaluation data about the visual performance of the test subject contains evaluation data about strabismus of the test subject. The evaluation data about strabismus contains evaluation data indicating whether or not the test subject has strabismus and evaluation data indicating the angle of strabismus.

The memory unit 220 is used to store the computer program 20C and a variety of data.

The output control unit 222 outputs data to at least one of the display device 101, the output device 50, or the audio output device 70. In the first embodiment, the output control unit 222 displays at least the evaluation data about the visual performance of the test subject in the display device 101 or the output device 50.

[Principle of Eye Gaze Detection]

Given below is the explanation of the principle of eye gaze detection according to the first embodiment. The following explanation is given mainly about the operations performed by the center-of-curvature calculating unit 214. The center-of-curvature calculating unit 214 calculates the position data of the corneal curvature centers 110 of the eyes 111 based on the image data of the eyes 111.

Figure 5:
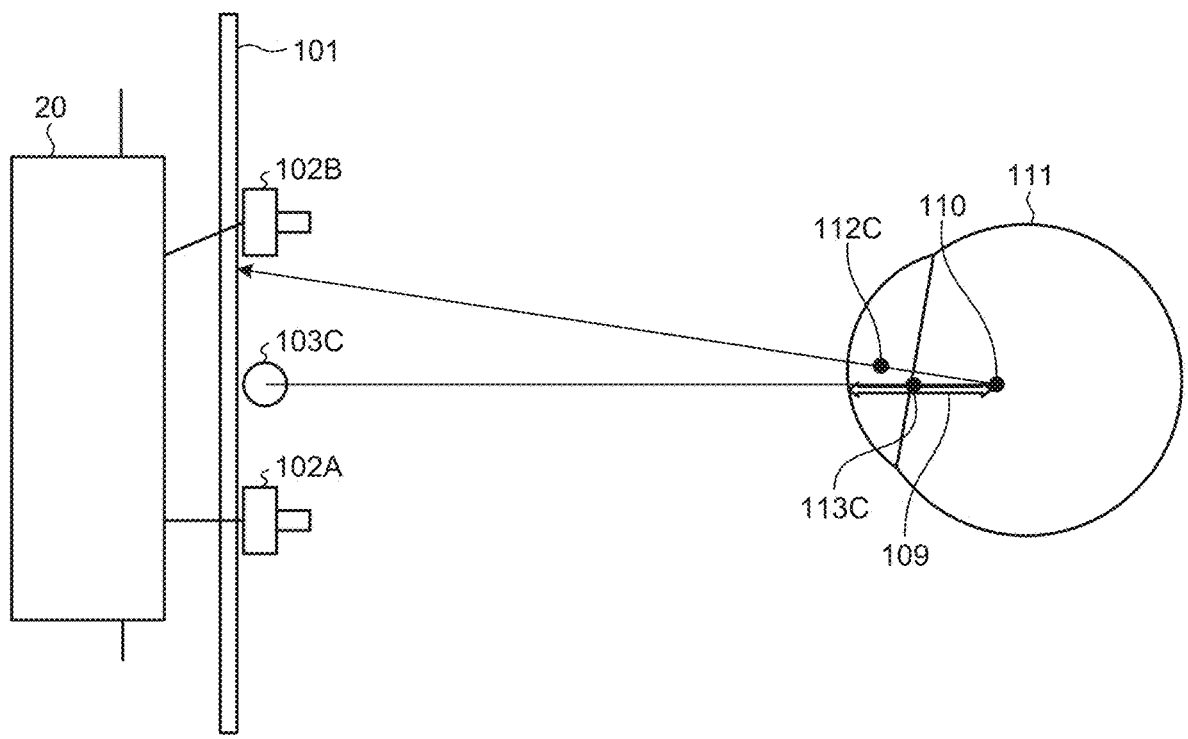
FIG. 5 is a schematic diagram for explaining a calculation method for calculating the position data of each corneal curvature center according to the first embodiment.
Figure 6:
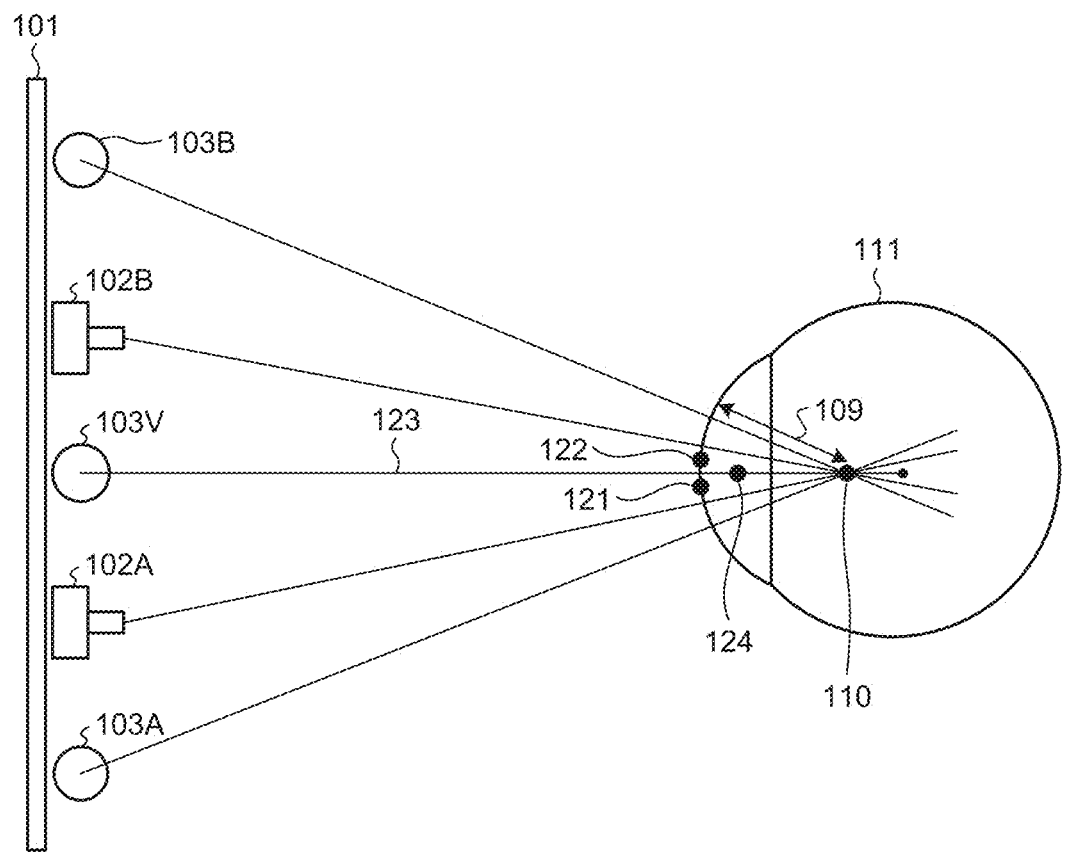
FIG. 6 is a schematic diagram for explaining the calculation method for calculating the position data of each corneal curvature center according to the first embodiment.

FIGS. 5 and 6 are schematic diagrams for explaining a calculation method for calculating the position data of each corneal curvature center 110 according to the first embodiment. FIG. 5 illustrates an example in which each eye 111 is lit up with a single light source 103C. FIG. 6 illustrates an example in which each eye 111 is lit up with the first light source 103A and the second light source 103B.

Firstly, the explanation is given about the example illustrated in FIG. 5. The light source 103C is disposed in between the first camera 102A and the second camera 102B. With reference to FIG. 5, the pupil center 112C represents the pupil center at the time when the eye 111 is lit up with the single light source 103C. The corneal reflex center 113C represents the corneal reflex center at the time when the eye 111 is lit up with the single light source 103C.

The corneal reflex center 113C is present on the straight line joining the light source 103C and the corneal curvature center 110. The corneal reflex center 113C is positioned at an intermediate point between the corneal surface and the corneal curvature center 110. A corneal curvature radius 109 represents the distance between the corneal surface and the corneal curvature center 110.

The position data of the corneal reflex center 113C is detected by the stereo camera device 102. The corneal curvature center 110 is present on the straight line joining the light source 103C and the corneal reflex center 113C. The center-of-curvature calculating unit 214 calculates, as the position data of the corneal curvature center 110, the position data at which the distance from the corneal reflex center 113C on the straight line becomes equal to a predetermined value. The predetermined value is determined in advance from the curvature radius of a common cornea or the like, and is stored in the memory unit 220.

Given below is the explanation of the example illustrated in FIG. 6. In the first embodiment, the pair of the first camera 102A and the second light source 103B and the pair of the second camera 102B and the first light source 103A are disposed at bilaterally symmetric positions with respect to a straight line passing through an intermediate position between the first camera 102A and the second camera 102B. It can be considered that a virtual light source 103V is present at an intermediate position between the first camera 102A and the second camera 102B.

A corneal reflex center 121 represents the corneal reflex center in the image of each eye 111 taken by the second camera 102B. Moreover, a corneal reflex center 122 represents the corneal reflex center in the image of each eye 111 taken by the first camera 102A. Furthermore, a corneal reflex center 124 represents the corneal reflex center corresponding to the virtual light source 103V.

The position data of the corneal reflex center 124 is calculated based on the position data of the corneal reflex center 121 and the position data of the corneal reflex center 122 as obtained by the stereo camera device 102. The stereo camera device 102 detects the position data of the corneal reflex center 121 and the position data of the corneal reflex center 122 in a local coordinate system that is defined in the stereo camera device 102. Regarding the stereo camera device 102, camera calibration based on a stereo calibration method is performed in advance, and a conversion parameter for converting the three-dimensional local coordinate system of the stereo camera device 102 into the three-dimensional global coordinate system is calculated. The conversion parameter is stored in the memory unit 220.

The center-of-curvature calculating unit 214 uses the conversion parameter and converts the position data of the corneal reflex center 121 and the position data of the corneal reflex center 122, which are obtained by the stereo camera device 102, into position data in the global coordinate system. Moreover, based on the position data of the corneal reflex center 121 and the position data of the corneal reflex center 122 that are defined in the global coordinate system, the center-of-curvature calculating unit 214 calculates the position data of the corneal reflex center 124 in the global coordinate system.

The corneal curvature center 110 is present on the straight line joining the virtual light source 103V and the corneal reflex center 124. The center-of-curvature calculating unit 214 calculates, as the position data of the corneal curvature center 110, the position data at which the distance from the corneal reflex center 124 on a straight line 123 becomes equal to a predetermined value. The predetermined value is determined in advance from the curvature radius of a common cornea or the like, and is stored in the memory unit 220.

As explained with reference to FIG. 6, even when two light sources are used, the corneal curvature center 110 is calculated according to an identical method to the method implemented in the case in which a single light source is used.

The corneal curvature radius 109 represents the distance between the corneal surface and the corneal curvature center 110. Thus, when the position data of the corneal surface and the position data of the corneal curvature center 110 are calculated, the corneal curvature radius 109 gets calculated.

In this way, in the first embodiment, the position data of the corneal curvature center 110 in the global coordinate system is calculated; the position data of the pupil center 112C is calculated; and the position data of the corneal reflex center 113C is calculated.

Based on the position data of the pupil center 112C and the position data of the corneal curvature center 110, the eye gaze detecting unit 216 can detect the eye gaze vectors of the test subject.

[Visual Performance Examination Method]

Figure 7:
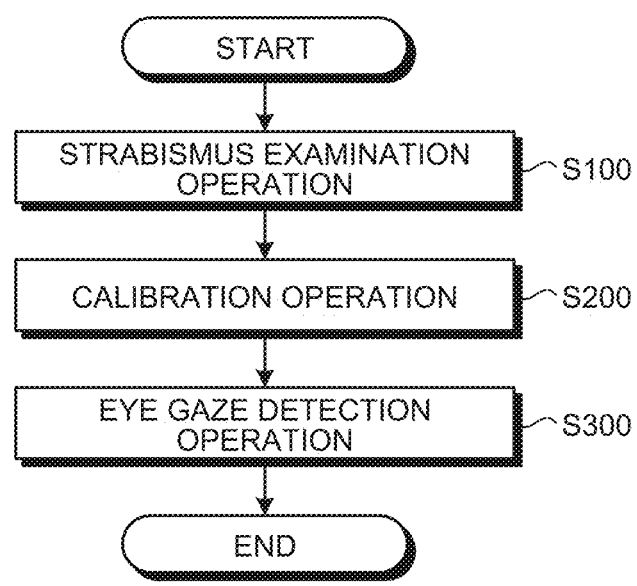
FIG. 7 is a flowchart for explaining an example of a visual performance examination method according to the first embodiment.

Given below is the explanation of an example of a visual performance examination method according to the first embodiment. FIG. 7 is a flowchart for explaining an example of the visual performance examination method according to the first embodiment. In the first embodiment, following operations are performed: a strabismus examination operation (Step S100) for examining strabismus of the test subject; a calibration operation (Step S200) that includes a calculation operation for calculating the position data of the corneal curvature center 110 and a calculation operation for calculating distance data between the pupil center 112C and the corneal curvature center 110; and an eye gaze detection operation (Step S300).

(Strabismus Examination Operation)

Given below is the explanation of a strabismus examination operation. In the first embodiment, in the visual performance examination device 100, the detection light emitted from the light source 103 is delivered to the test subject; the eyes 111 of the test subject that are irradiated with the detection light are captured by the stereo camera device 102; and the state of strabismus of the test subject is examined based on the position data of the corneal reflexes 113 that represent the reflected images of the light source 103 on the corneal surfaces.

Figure 8:
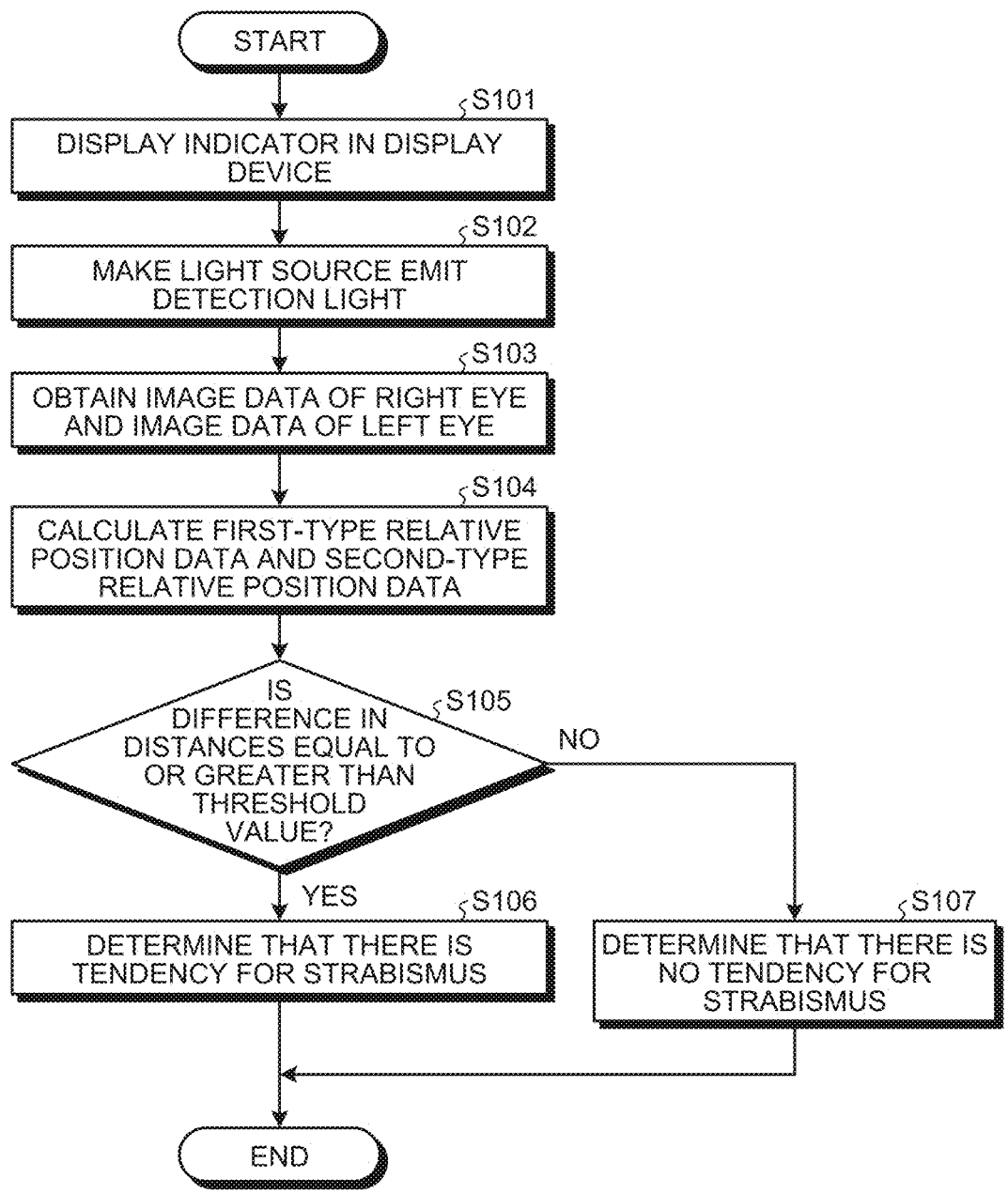
FIG. 8 is a flowchart for explaining an example of a strabismus examination operation performed according to the first embodiment.

FIG. 8 is a flowchart for explaining an example of the strabismus examination operation (Step S100) performed according to the first embodiment. As illustrated in FIG. 8, the strabismus examination operation (Step S100) includes the following steps: a step for displaying the indicator 130, on which the test subject is to be made to fix the eyes, in the display device 101 (Step S101); a step for irradiating the test subject with the detection light emitted from the light source 103 (Step S102); a step for obtaining the image data of the right eye 111R and the image data of the left eye 111L of the test subject who is irradiated with the detection light emitted from the light source 103 (Step S103); a step for calculating, based on the image data of the right eye 111R, the first-type relative position data that indicates the relative position between the pupil 112R of the right eye 111R and the corneal reflex 113R of the right eye 111R, and calculating, based on the image data of the left eye 111L, the second-type relative position data that indicates the relative position between the pupil 112L of the left eye 111L and the corneal reflex 113L of the left eye 111L (Step S104); and steps for evaluating the visual performance of the test subject based on the first-type relative position data and the second-type relative position data, and outputting evaluation data (Step S105, Step S106, and Step S107).

The display control unit 208 displays the indicator 130, on which the test subject is to be made to fix the eyes, in the display device 101 (Step S101). For example, the display control unit 208 displays the indicator 130 at the center of the display screen 101S. In the first embodiment, the display control unit 208 displays, in the display device 101, the indicator 130 that remains stationary in the display screen 101S. The test subject is instructed to focus on the indicator 130 displayed in the display device 101.

The detection light is emitted from the light source 103 (Step S102). Then, the image data of the right eye 111R and the image data of the left eye 111L of the test subject, who is irradiated with the detection light, are obtained by the stereo camera device 102. The image data of the eyes 111 of the test subject is obtained by at least either the first camera 102A or the second camera 102B. In the first embodiment, the image data of the eyes 111 of the test subject is obtained by the first camera 102A. Alternatively, the image data of the eyes 111 of the test subject may be obtained by the second camera 102B. Still alternatively, the image data obtained by the first camera 102A and the image data obtained by the second camera 102B may be used together.

Figure 9:
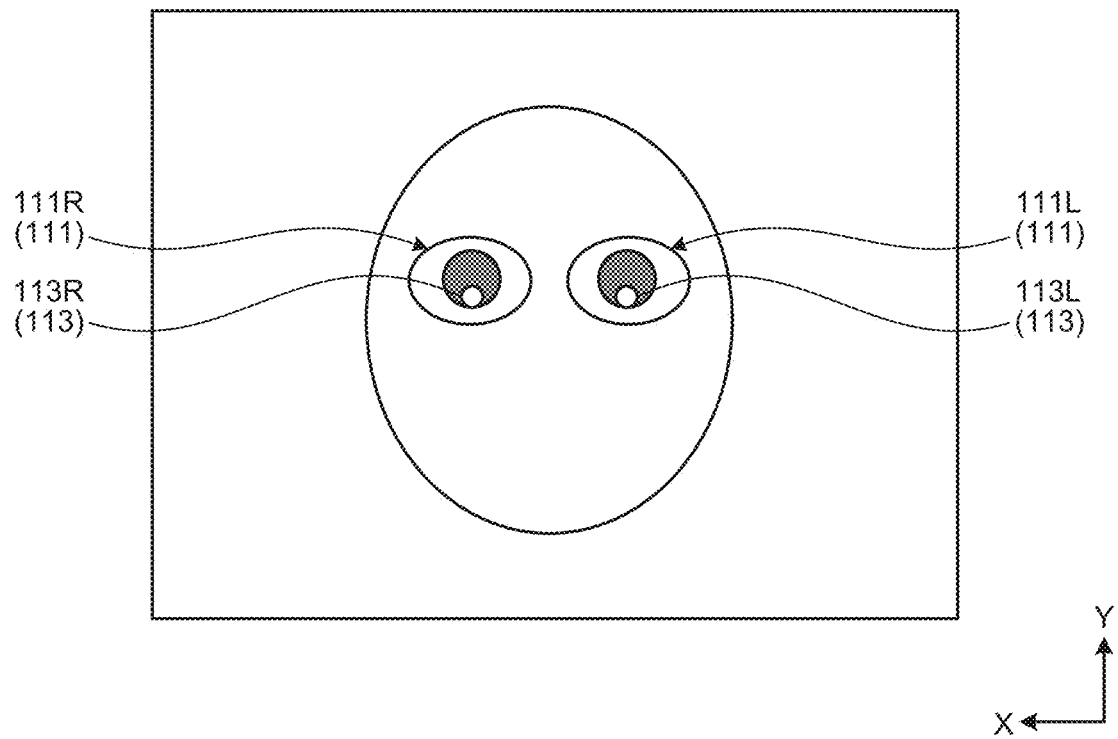
FIG. 9 is a diagram that schematically illustrates an example of the test subject who is irradiated with a detection light according to the first embodiment.

FIG. 9 is a diagram that schematically illustrates an example of the test subject who is irradiated with the detection light according to the first embodiment. As illustrated in FIG. 9, as a result of formation of the detection light in each of the right eye 111R as well as the left eye 111L of the test subject, the corneal reflex 113R is formed in the right eye 111R and the corneal reflex 113L is formed in the left eye 111L.

The image data obtaining unit 202 obtains the image data of the right eye 111R and the image data of the left eye 111L of the test subject, who is irradiated with the detection light, from the stereo camera device 102 (Step S103).

Figure 10:
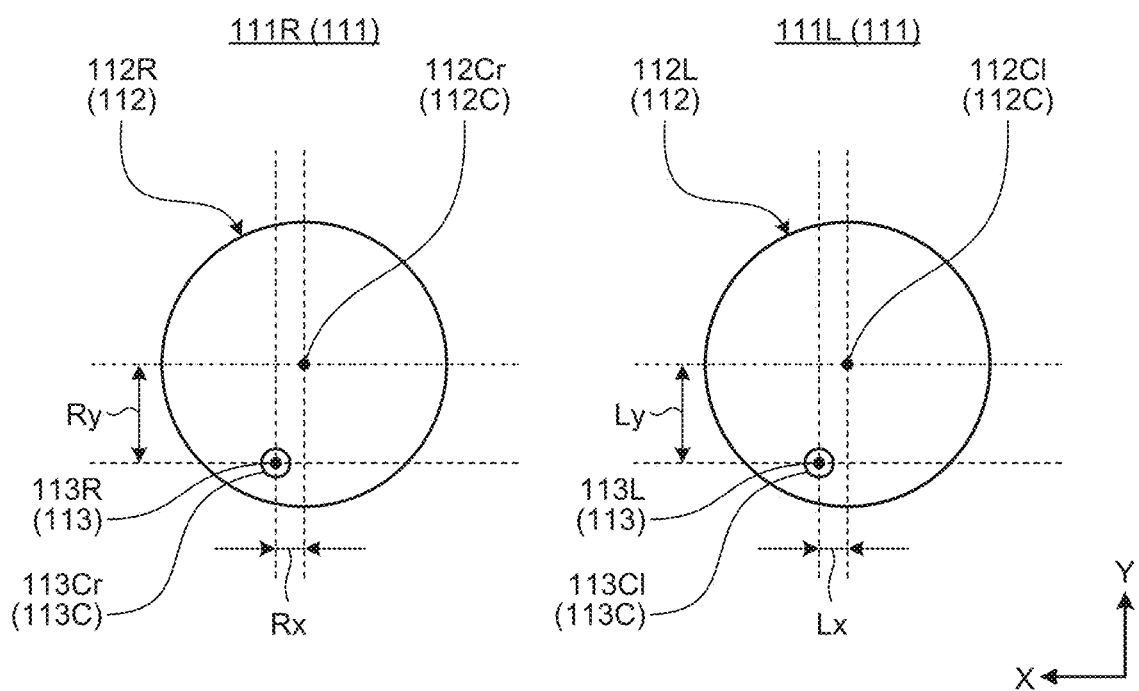
FIG. 10 is a diagram that schematically illustrates an example of the image data of the eyes of a test subject who does not have the tendency for strabismus.

FIG. 10 is a diagram that schematically illustrates an example of the image data obtained by the image data obtaining unit 202 according to the first embodiment. As illustrated in FIG. 10, the image data contains the following: the image data of the pupil 112R of the right eye 111R; the image data of the corneal reflex 113R of the right eye 111R; the image data of the pupil 112L of the left eye 111L; and the image data of the corneal reflex 113L of the left eye 111L.

The position calculating unit 212 calculates, based on the image data of the right eye 111R, position data of a pupil center 112Cr of the right eye 111R and position data of a corneal reflex center 113Cr of the right eye 111R in the X-Y plane. Moreover, the position calculating unit 212 calculates, based on the image data of the left eye 111L, position data of a pupil center 112C1 of the left eye 111L and position data of a corneal reflex center 113C1 of the left eye 111L in the X-Y plane.

The position calculating unit 212 calculates, based on the position data of the pupil center 112Cr of the right eye 111R and the position data of the corneal reflex center 113Cr of the right eye 111R in the X-Y plane, first-type relative position data that indicates the relative position between the pupil center 112Cr of the right eye 111R and the corneal reflex center 113Cr of the right eye 111R in the X-Y plane. Moreover, the position calculating unit 212 calculates, based on the position data of the pupil center 112C1 of the left eye 111L and the position data of the corneal reflex center 113C1 of the left eye 111L in the X-Y plane, second-type relative position data that indicates the relative position between the pupil center 112C1 of the left eye 111L and the corneal reflex center 113C1 of the left eye 111L in the X-Y plane (Step S104).

As illustrated in FIG. 10, in the first embodiment, the first-type relative position data contains a distance Rx between the pupil center 112Cr of the right eye 111R and the corneal reflex center 113Cr of the right eye 111R in the X-axis direction, and contains a distance Ry between the pupil center 112Cr of the right eye 111R and the corneal reflex center 113Cr of the right eye 111R in the Y-axis direction. The second-type relative position data contains a distance Lx between the pupil center 112C1 of the left eye 111L and the corneal reflex center 113C1 of the left eye 111L in the X-axis direction, and contains a distance Ly between the pupil center 112C1 of the left eye 111L and the corneal reflex center 113C1 of the left eye 111L in the Y-axis direction.

The evaluating unit 218 calculates a difference Δx between the distance Rx and the distance Lx, and calculates a difference Δy between the distance Ry and the distance Ly.

Then, the evaluating unit 218 determines whether or not the difference Δx between the distance Rx and the distance Lx is equal to or greater than a threshold value SHx. Moreover, the evaluating unit 218 determines whether or not the difference Δy between the distance Ry and the distance Ly is equal to or greater than a threshold value SHy (Step S105). That is, the evaluating unit 218 determines whether or not Equation (1A) and Equation (1B) hold true.

$$|Lx-Rx|<SHx \qquad (1A)$$

$$|Ly-Ry|<SHy \qquad (1B)$$

Figure 11:
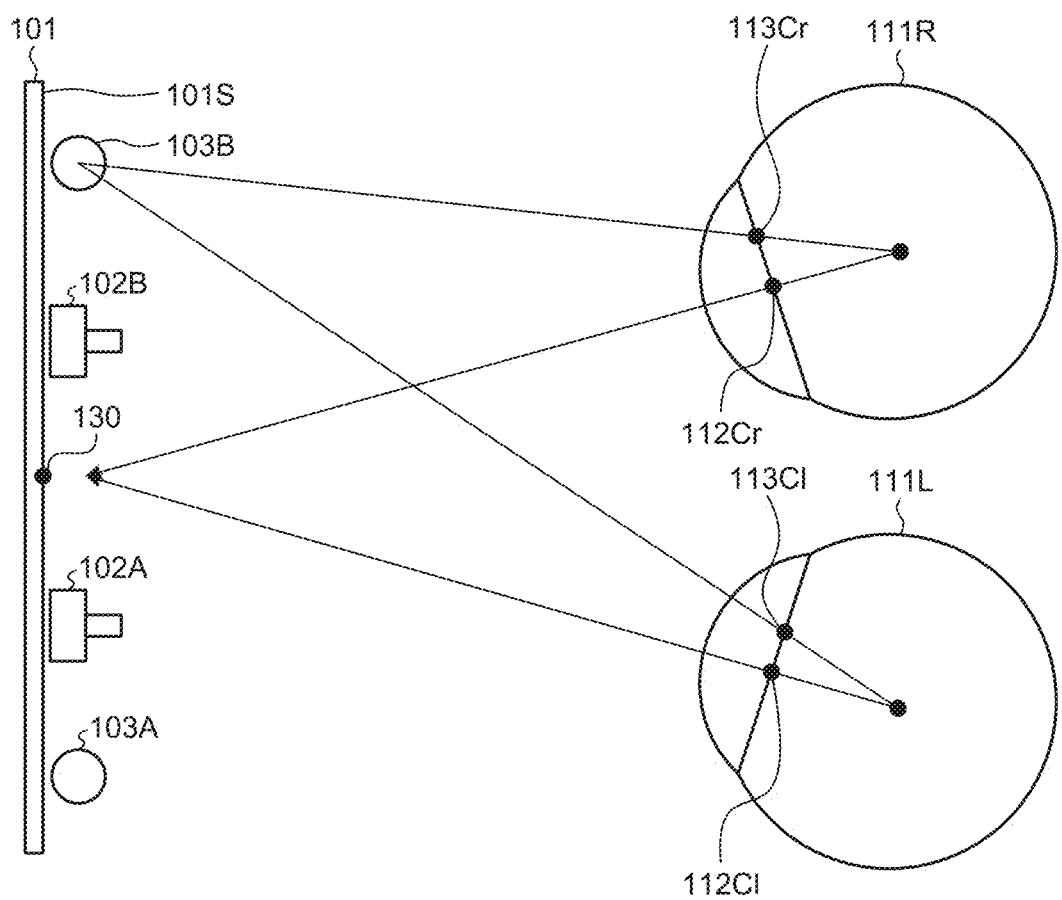
FIG. 11 is a diagram that schematically illustrates the eye gaze of the test subject, who does not have the tendency for strabismus, at the time of focusing on an indicator being displayed at the center of the display screen of the display device.
Figure 12:
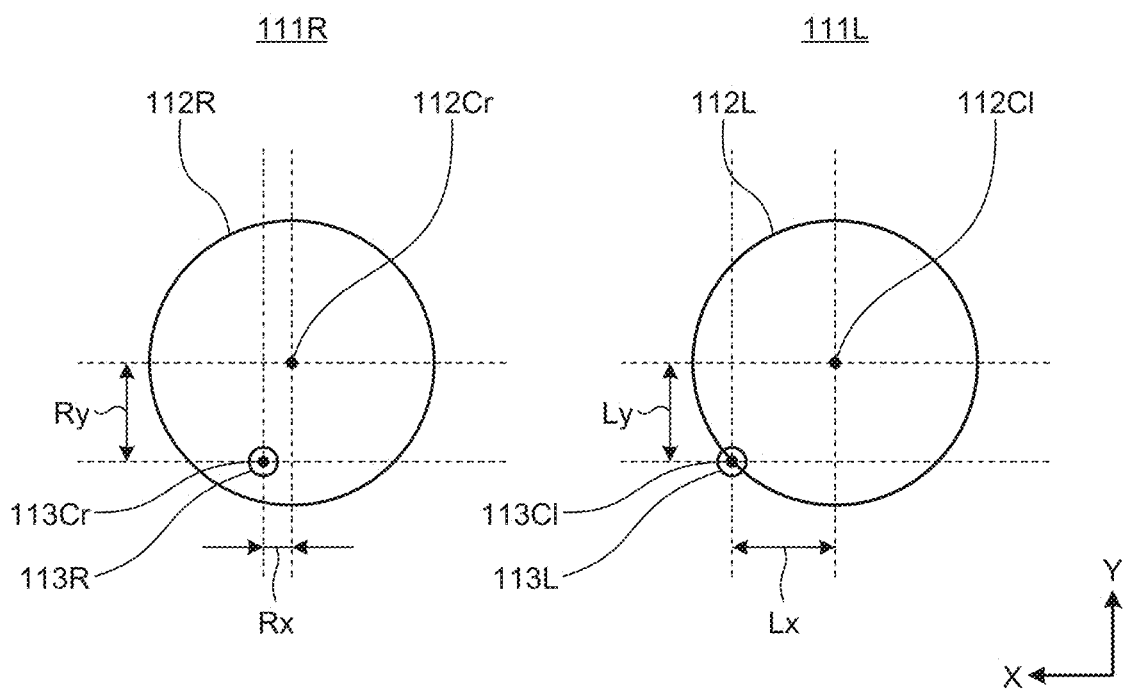
FIG. 12 is a diagram that schematically illustrates an example of the image data of the eyes of a test subject who has the tendency for strabismus.
Figure 13:
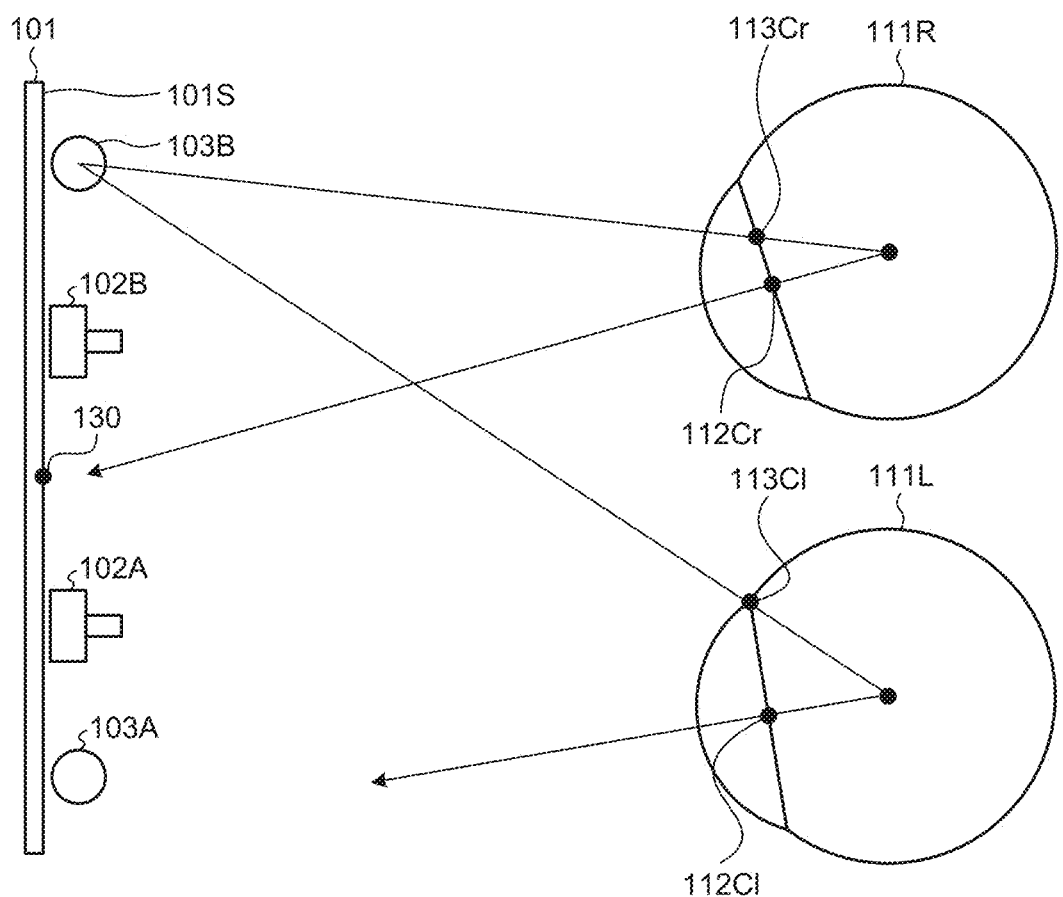
FIG. 13 is a diagram that schematically illustrates the eye gaze of the test subject, who has the tendency for strabismus, at the time of focusing on the indicator being displayed at the center of the display screen of the display device.

FIG. 10 is a diagram that schematically illustrates an example of the image data of the eyes 111 of the test subject who does not have the tendency for strabismus. FIG. 11 is a diagram that schematically illustrates the eye gaze of a test subject, who does not have the tendency for strabismus, at the time of focusing on the indicator 130 being displayed at the center of the display screen 101S of the display device 101. FIG. 12 is a diagram that schematically illustrates an example of the image data of the eyes 111 of a test subject who has the tendency for strabismus. FIG. 13 is a diagram that schematically illustrates the eye gaze of the test subject, who has the tendency for strabismus, at the time of focusing on the indicator 130 being displayed at the center of the display screen 101S of the display device 101.

As illustrated in FIG. 11, when the test subject does not have the tendency for strabismus, the eye gaze of the right eye 111R as well as the eye gaze of the left eye 111L is directed toward the indicator 130. However, as illustrated in FIG. 13, when the test subject has the tendency for strabismus, at least either the eye gaze of the right eye 111R or the eye gaze of the left eye 111L deviates away from the indicator 130. FIG. 13 illustrates the state in which the left eye 111L of the test subject has the tendency for strabismus. As illustrated in FIG. 10, when the test subject does not have the tendency for strabismus, the difference Δx between the distance Rx and the distance Lx is small, and the difference Δy between the distance Ry and the distance Ly is also small. On the other hand, as illustrated in FIG. 12, when the test subject has the tendency for strabismus, at least either the difference Δx between the distance Rx and the distance Lx is large or the difference Δy between the distance Ry and the distance Ly is large.

At Step S105, if it is either determined that the difference Δx is equal to or greater than the threshold value SHx or determined that the difference Δy is equal to or greater than the threshold value SHy (Yes at Step S105), then the evaluating unit 218 outputs evaluation data indicating that there is abnormality in the visual performance of the test subject (Step S106). That is, when at least either Equation (1A) or Equation (1B) does not hold true, the evaluating unit 218 determines that the test subject has the tendency for strabismus and outputs data indicating that the test subject has the tendency for strabismus.

On the other hand, at Step S105, if it is determined that the difference Δx is not equal to or greater than the threshold value SHx and determined that the difference Δy is not equal to or greater than the threshold value SHy (No at Step S105), then the evaluating unit 218 outputs the evaluation data indicating that there is no abnormality in the visual performance of the test subject (Step S107). That is, when Equation (1A) as well as Equation (1B) holds true, the evaluating unit 218 determines that the test subject does not have the tendency for strabismus and outputs the evaluation data indicating that the test subject does not have the tendency for strabismus.

Herein, the threshold value SHx and the threshold value SHy are derived either statistically or empirically based on the data obtained from a plurality of test subjects who have the tendency for strabismus, and are stored in the memory unit 220. In the first embodiment, the threshold value SHx and the threshold value SHy are set to values in the range from equal to or greater than 3 [%] of the diameter of the pupil 112 to equal to or smaller than 7 [%] of the diameter of the pupil 112. Thus, for example, the threshold value SHx and the threshold value SHy can be set to values in the range from equal to or greater than 0.07 [mm] to equal to or smaller than 0.13 [mm].

In the first embodiment, if the difference Δx is equal to or greater than the threshold value SHx, then the test subject is evaluated to have the tendency for esotropia or exotropia. If the difference Δy is equal to or greater than the threshold value SHy, then the test subject is evaluated to have the tendency for hypertropia or hypotropia.

The output control unit 222 outputs, to the display device 101 or the output device 50, either the evaluation data indicating the tendency for strabismus or the evaluation data indicating no tendency for strabismus.

It marks the end of the strabismus examination operation.

(Calibration Operation)

Given below is the explanation of the calibration operation. In the first embodiment, after the strabismus examination operation (Step S100) is performed, the calibration operation is performed (Step S200) that includes a calculation operation for calculating the position data of the corneal curvature centers 110 and a calculation operation for calculating the distance data between the pupil centers 112C and the corneal curvature centers 110.

Figure 14:
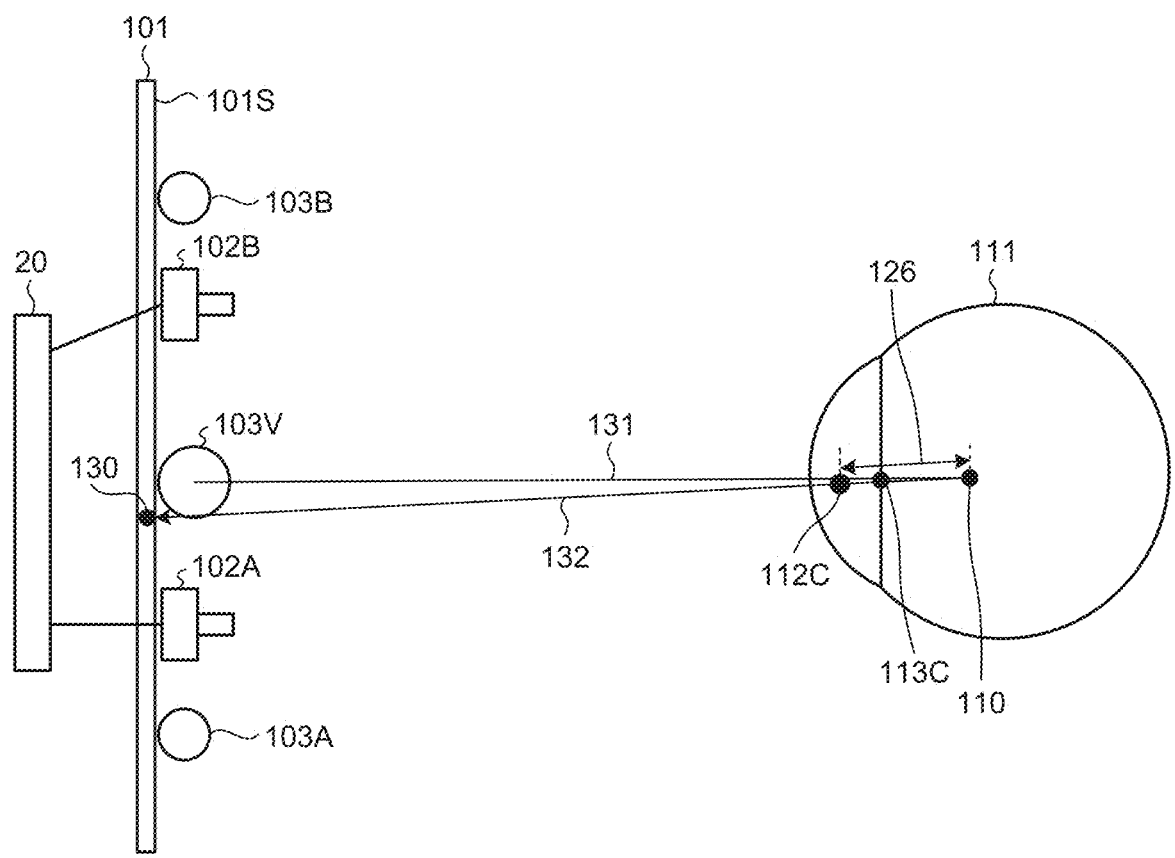
FIG. 14 is a schematic diagram for explaining an example of a calibration operation performed according to the first embodiment.

FIG. 14 is a schematic diagram for explaining an example of the calibration operation performed according to the first embodiment. The calibration operation includes calculating the position data of the corneal curvature center 110 and calculating a distance 126 between the pupil center 112C and the corneal curvature center 110.

The display control unit 208 displays the indicator 130, on which the test subject is to be made to fix the eyes, in the display device 101. The indicator 130 is defined in the global coordinate system. In the first embodiment, for example, the indicator 130 is displayed at the center of the display screen 101S of the display device 101. Alternatively, the indicator 130 may be displayed at an end portion of the display screen 101S.

A straight line 131 joins the virtual light source 103V and the corneal reflex center 113C. A straight line 132 joins the indicator 130 and the pupil center 112C. The corneal curvature center 110 represents the point of intersection between the straight lines 131 and 132. The center-of-curvature calculating unit 214 can calculate the position data of the corneal curvature center 110 based on the following: the position data of the virtual light source 103V; the position data of the indicator 130; the position data of the pupil center 112C; and the position data of the corneal reflex center 113C.

Figure 15:
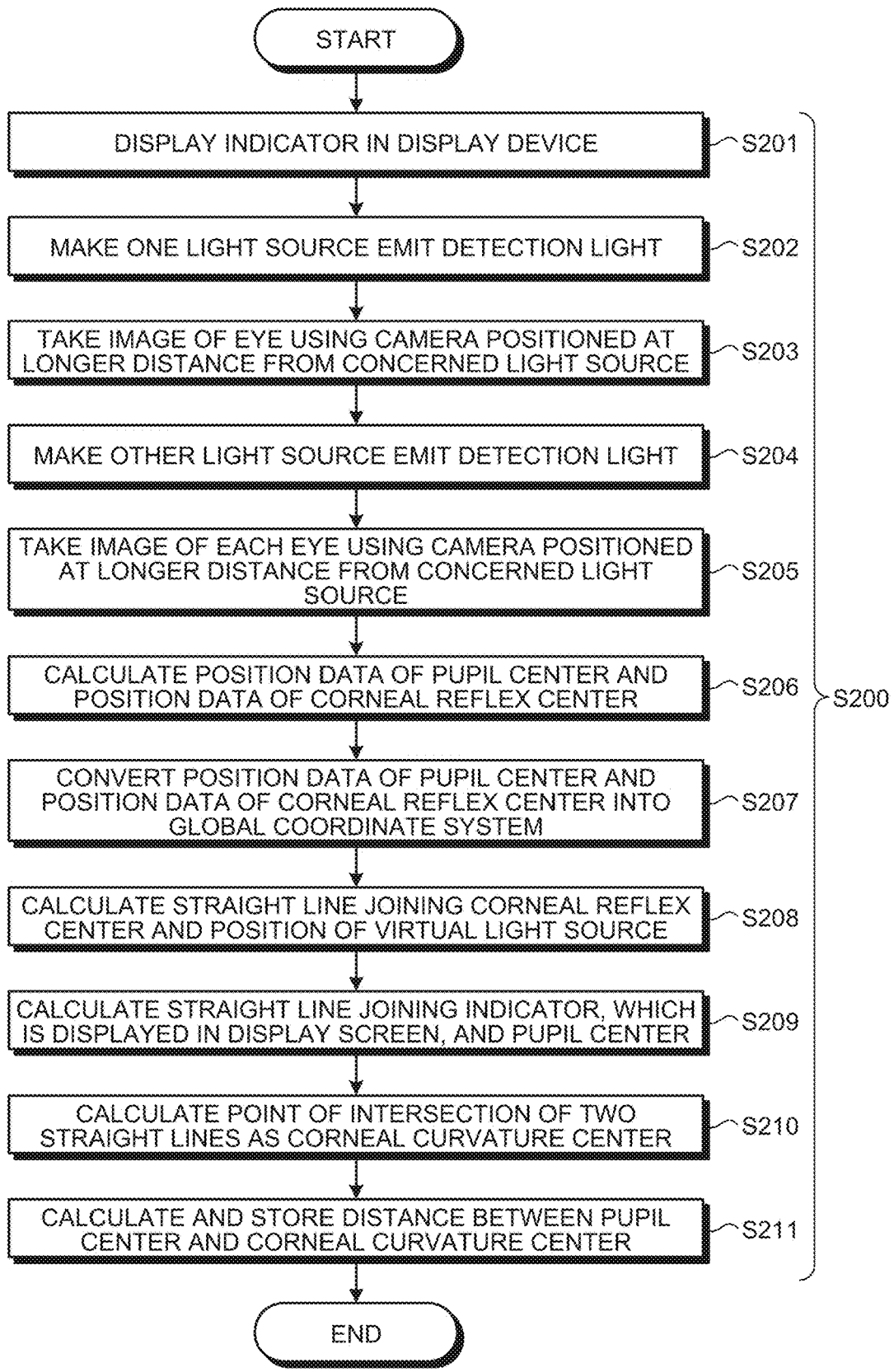
FIG. 15 is a flowchart for explaining an example of the calibration operation performed according to the first embodiment.

FIG. 15 is a flowchart for explaining an example of the calibration operation (Step S200) performed according to the first embodiment. The output control unit 222 displays the indicator 130 in the display screen 101S of the display device 101 (Step S201). Thus, the test subject becomes able to fix the eyes on the indicator 130.

Then, the light source control unit 210 controls the light source driving unit 406 and makes either the first light source 103A or the second light source 103B emit the detection light (Step S202). Subsequently, the stereo camera device 102 takes an image of each eye 111 of the test subject using the camera, from among the first camera 102A and the second camera 102B, that is positioned at a longer distance from the light source which emitted the detection light (Step S203).

Then, the light source control unit 210 controls the light source driving unit 406 and makes the other light source, from among the first light source 103A and the second light source 103B, emit the detection light (Step S204). Subsequently, the stereo camera device 102 takes an image of the eye 111 of the test subject using the camera, from among the first camera 102A and the second camera 102B, that is positioned at a longer distance from the light source which emitted the detection light (Step S205).

The stereo camera device 102 detects the pupil 112 as a dark portion and detects the corneal reflex 113 as a bright portion. That is, the image of the pupil 112 obtained in the stereo camera device 102 becomes a low-brightness image, and the image of the corneal reflex 113 obtained in the stereo camera device 102 becomes a high-brightness image. Based on the brightness of the obtained images, the position calculating unit 212 can detect the position data of the pupil 112 and the position data of the corneal reflex 113. Moreover, based on the image data of the pupil 112, the position calculating unit 212 calculates the position data of the pupil center 112C. Furthermore, based on the image data of the corneal reflex 113, the position calculating unit 212 calculates the position data of the corneal reflex center 113C (Step S206).

The position data detected by the stereo camera device 102 represents the position data defined in the local coordinate system. Hence, the position calculating unit 212 uses the conversion parameter stored in the memory unit 220; performs coordinate conversion of the position data of the pupil center 112C and the position data of the corneal reflex center 113C as detected by the stereo camera device 102; and calculates the position data of the pupil center 112C and the position data of the corneal reflex center 113C as defined in the global coordinate system (Step S207).

The center-of-curvature calculating unit 214 calculates the straight line 131 that joins the corneal reflex center 113C and the virtual light source 103V defined in the global coordinate system (Step S208).

Subsequently, the center-of-curvature calculating unit 214 calculates the straight line 132 that joins the indicator 130, which is displayed in the display screen 101S of the display device 101, and the pupil center 112C (Step S209). The center-of-curvature calculating unit 214 obtains the point of intersection between the straight line 131, which is calculated at Step S208, and the straight line 132, which is calculated at Step S209; and sets the point of intersection as the corneal curvature center 110 (Step S210).

Moreover, the center-of-curvature calculating unit 214 calculates the distance 126 between the pupil center 112C and the corneal curvature center 110, and stores the distance 126 in the memory unit 220 (Step S211). The stored distance is used in calculating the corneal curvature center 110 during the eye gaze detection operation performed at Step S300.

(Eye Gaze Detection Operation)

Given below is the explanation of the eye gaze detection operation. The eye gaze detection operation is performed after the calibration operation. The eye gaze detecting unit 216 calculates, based on the image data of the eyes 111, the eye gaze vectors and the position data of the point of regard of the test subject.

Figure 16:
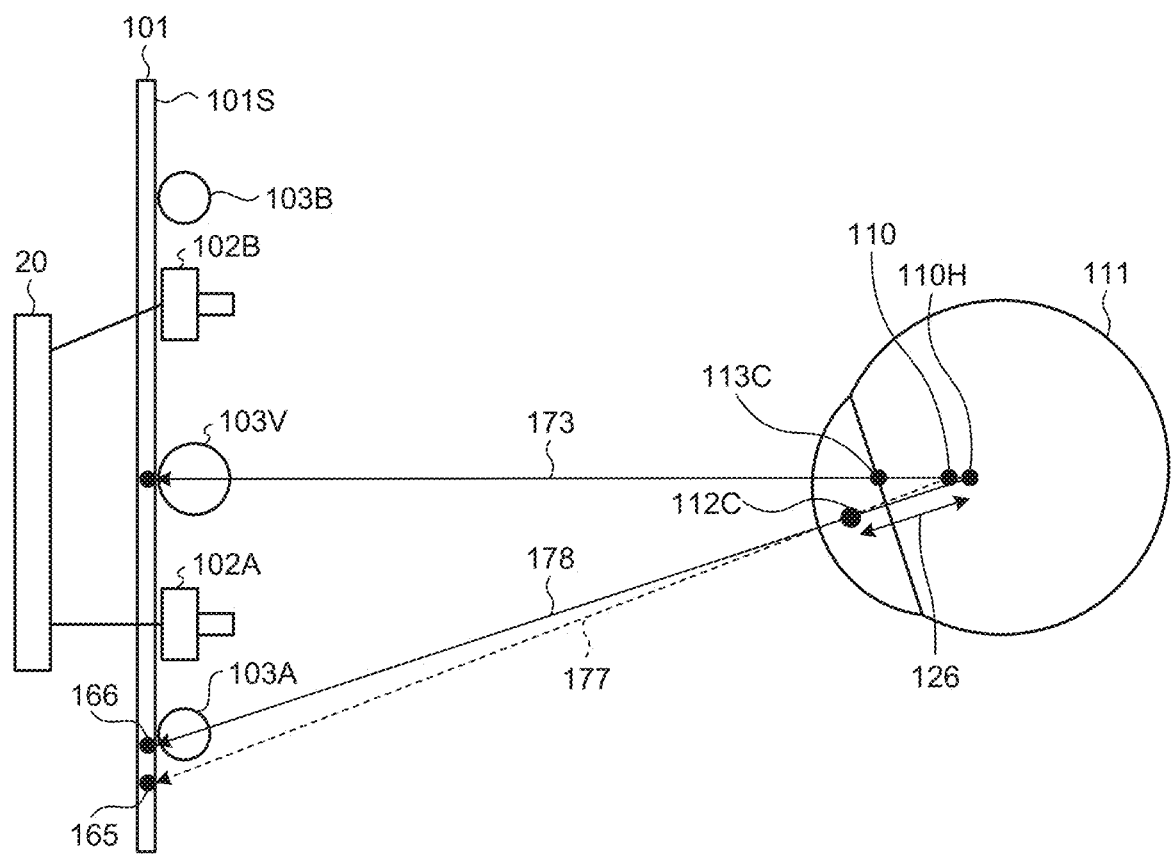
FIG. 16 is a schematic diagram for explaining an example of an eye gaze detection operation performed according to the first embodiment.

FIG. 16 is a schematic diagram for explaining an example of the eye gaze detection operation performed according to the first embodiment. The eye gaze detection operation includes correcting the position of each corneal curvature center 110 using the distance 126 between the corresponding pupil center 112C and the corresponding corneal curvature center 110 as obtained during the calibration operation (Step S200), and includes calculating the point of regard using the position data of the corrected corneal curvature center 110.

With reference to FIG. 16, a point of regard 165 represents the point of regard obtained according to the corneal curvature center 110 that is calculated using the common curvature radius. A point of regard 166 represents the point of regard obtained according to the corneal curvature center 110 that is calculated using the distance 126 obtained during the calibration operation.

The pupil center 112C represents the pupil center calculated during the calibration operation, and the corneal reflex center 113C represents the corneal reflex center calculated during the calibration operation.

A straight line 173 joins the virtual light source 103V and the corneal reflex center 113C. The corneal curvature center 110 represents the position of the corneal curvature center calculated using the common curvature radius.

The distance 126 represents the distance between the pupil center 112C and the corneal curvature center 110 as calculated during the calibration operation.

A corneal curvature center 110H represents the position of the post-correction corneal curvature center obtained by correcting the corneal curvature center 110 using the distance 126.

The corneal curvature center 110H is obtained according to the fact that the corneal curvature center 110 is present on the straight line 173 and the fact that the distance between the pupil center 112C and the corneal curvature center 110 is equal to the distance 126. As a result, an eye gaze 177 that gets calculated in the case of using the common curvature radius is corrected to an eye gaze 178. Moreover, the point of regard on the display screen 101S of the display device 101 gets corrected from the point of regard 165 to the point of regard 166.

Figure 17:
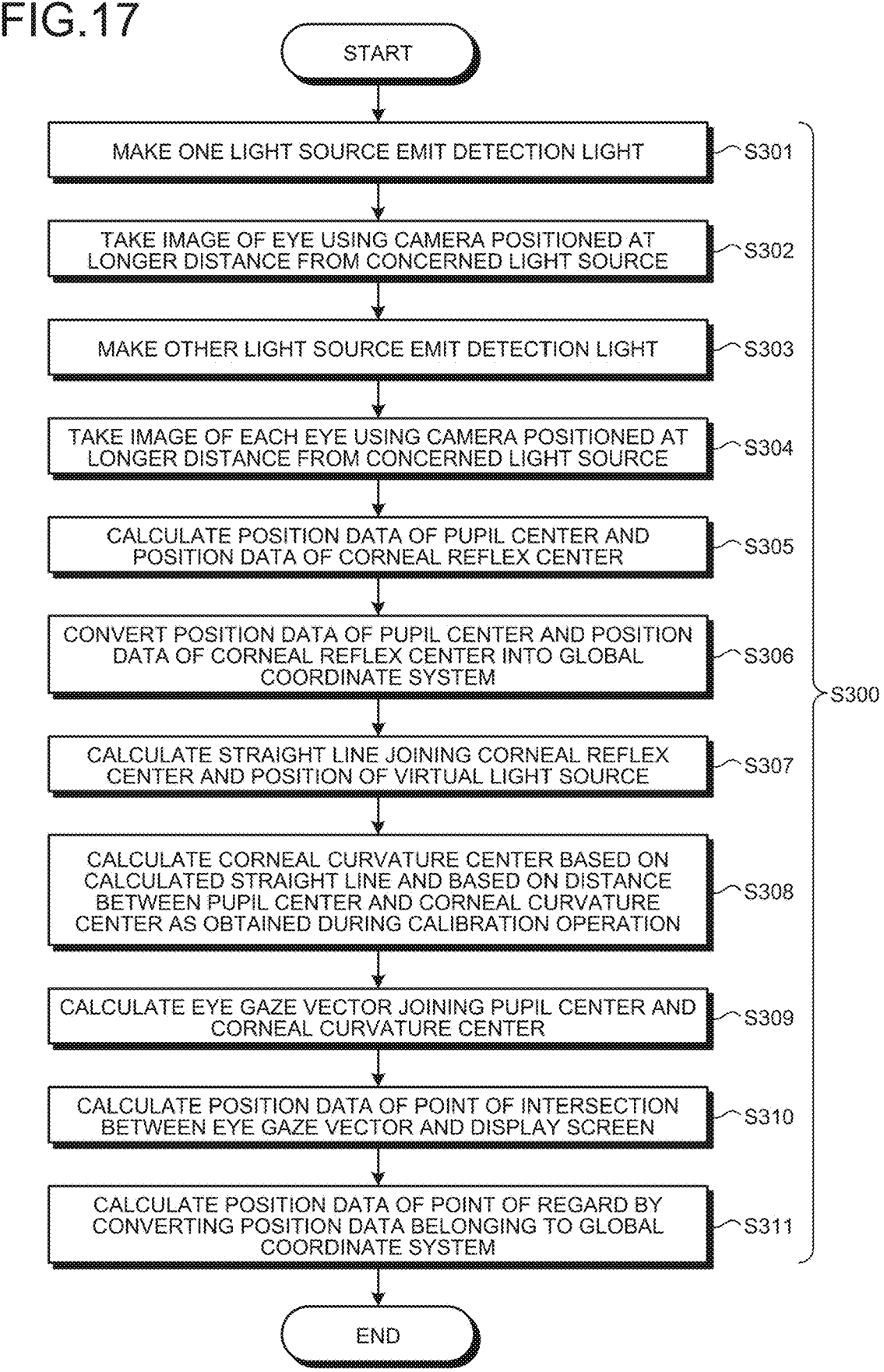
FIG. 17 is a flowchart for explaining an example of the eye gaze detection operation performed according to the first embodiment.

FIG. 17 is a flowchart for explaining an example of the eye gaze detection operation (Step S300) performed according to the first embodiment. With reference to FIG. 17, the operations performed from Step S301 to Step S307 are identical to the operations performed from S202 to Step S208 illustrated in FIG. 15. Hence, that explanation is not given again.

The center-of-curvature calculating unit 214 calculates, as the corneal curvature center 110H, such a position which is present on the straight line 173 calculated at Step S307 and which has the distance from the pupil center 112C to be equal to the distance 126 obtained during the calibration operation (Step S308).

The eye gaze detecting unit 216 calculates the eye gaze vector that joins the pupil center 112C and the corneal curvature center 110H (Step S309). The eye gaze vector indicates the eye gaze direction in which the test subject is looking at. Moreover, the eye gaze detecting unit 216 calculates the position data of the point of intersection between the eye gaze vector and the display screen 101S of the display device 101 (Step S310). The position data of the point of intersection between the eye gaze vector and the display screen 101S of the display device 101 represents the position data of the point of regard of the test subject in the display screen 101S defined in the global coordinate system.

The eye gaze detecting unit 216 converts the position data of the point of regard, which is defined in the global coordinate system, into the position data in the display screen 101S of the display device 101 that is defined in the two-dimensional coordinate system (Step S311). That results in the calculation of the position data of the point of regard in the display screen 101S of the display device 101 at which the test subject is looking.

[Actions and Effects]

As explained above, according to the first embodiment, the image data of the right eye 111R and the image data of the left eye 111L are obtained. Then, based on the image data of the right eye 111R, the first-type relative position data indicating the relative position between the pupil center 112Cr and the corneal reflex center 113Cr of the right eye 111R is calculated. Moreover, based on the image data of the left eye 111L, the second-type relative position data indicating the relative position between the pupil center 112C1 and the corneal reflex center 113C1 of the left eye 111L is calculated. After the first-type relative position data and the second-type relative position data are calculated, based on the first-type relative position data and the second-type relative position data, the evaluation data about the visual performance of the test subject is output. Since the status of strabismus of the test subject is evaluated based on the first-type relative position data regarding the right eye 111R and the second-type relative position data regarding the left eye 111L; even if there is a change in the relative position between the light source 103 and the test subject during the strabismus examination, the examination accuracy is prevented from undergoing a decline. That is, during the strabismus examination, if the head portion of the test subject moves, the right eye 111R and the left eye 111L move while maintaining the relative position therebetween. Thus, even if the head portion of the test subject moves, the relative position between the right eye 111R and the left eye 111L is maintained, so that the state of strabismus of the test subject can be accurately examined based on the first-type relative position data regarding the right eye 111R and the second-type relative position data regarding the left eye 111L.

Moreover, in the first embodiment, the distances Rx and Ry are calculated as the first-type relative position data, and the distances Lx and Ly are calculated as the second-type relative position data. Based on the difference Δx between the distances Rx and Lx and based on the difference Δy between the distances Ry and Ly, the evaluating unit 218 outputs the evaluation data. As a result, it becomes possible to evaluate whether or not the test subject has the tendency for esotropia or exotropia, and to evaluate whether or not the test subject has the tendency for hypertropia or hypotropia. For example, if the difference Δx is equal to or greater than the threshold value SHx, then it can be evaluated that the test subject has the tendency for esotropia or exotropia. Similarly, if the difference Δy is equal to or greater than the threshold value SHy, then it can be evaluated that the test subject has the tendency for hypertropia or hypotropia.

Second Embodiment

Given below is the explanation of a second embodiment. In the following explanation, the constituent elements that are identical or equivalent to the first embodiment are referred to by the same reference numerals, and their explanation is either simplified or omitted.

In the second embodiment, the explanation is given about an example in which, during the strabismus detection operation (Step S100), based on the first-type relative position data and the second-type relative position data, a distance D between the corneal reflex center 113Cr of the right eye 111R and the corneal reflex center 113C1 of the left eye 111L is calculated when the position of the pupil center 112Cr of the right eye 111R and the position of the pupil center 112C1 of the left eye 111L are set to be coincident in the X-Y plane.

Figure 18:
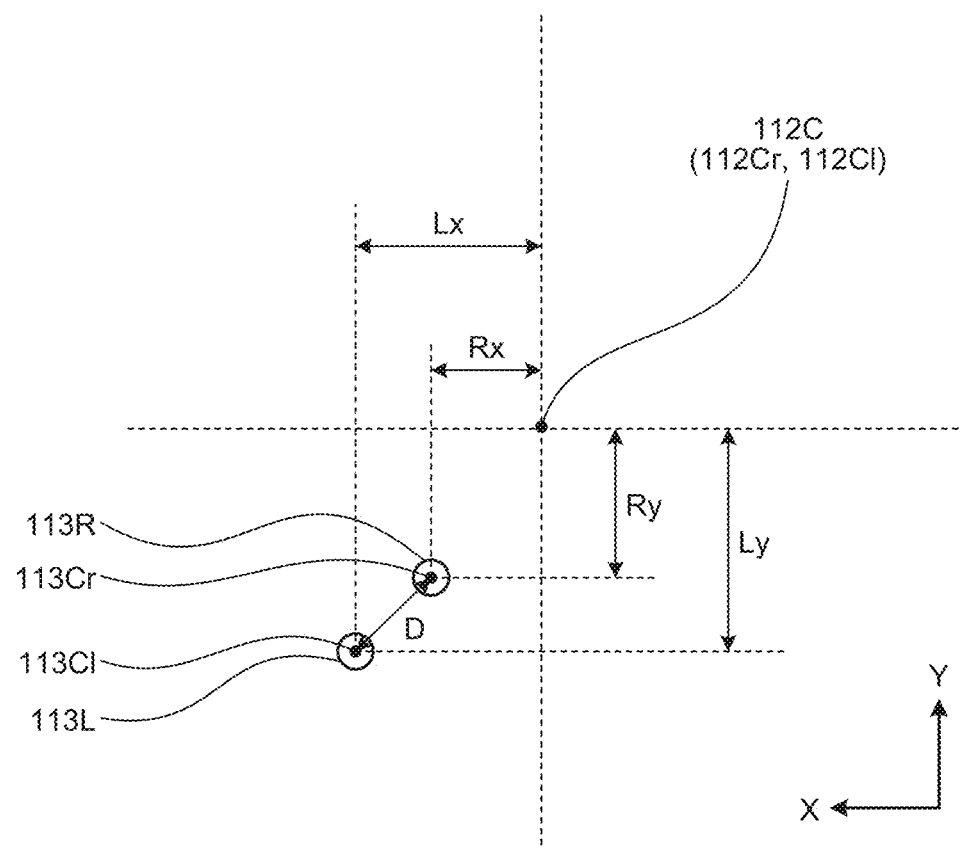
FIG. 18 is a diagram that schematically illustrates an example of the result of performing image processing with respect to the image data of the right eye and the image data of the left eye according to a second embodiment.

FIG. 18 is a diagram that schematically illustrates an example of the result of performing image processing with respect to the image data of the right eye 111R and the image data of the left eye 111L according to the second embodiment. The image processing unit 206 synthesizes the image data of the right eye 111R and the image data of the left eye 111L, which are obtained by the image data obtaining unit 202, in such a way that the position of the pupil center 112Cr of the right eye 111R and the position of the pupil center 112C1 of the left eye 111L become coincident in the X-Y plane.

The position calculating unit 212 calculates, from the image data synthesized by the image processing unit 206, the position data of the pupil center 112Cr of the right eye 111R and the position data of the corneal reflex center 113Cr of the right eye 111R in the X-Y plane. Similarly, the position calculating unit 212 calculates, from the image data synthesized by the image processing unit 206, the position data of the pupil center 112C1 of the left eye 111L and the position data of the corneal reflex center 113C1 of the left eye 111L in the X-Y plane.

Moreover, the position calculating unit 212 calculates the distance Rx between the pupil center 112Cr of the right eye 111R and the corneal reflex center 113Cr of the right eye 111R in the X-axis direction, and calculates the distance Ry between the pupil center 112Cr of the right eye 111R and the corneal reflex center 113Cr of the right eye 111R in the Y-axis direction. Furthermore, the position calculating unit 212 calculates the distance Lx between the pupil center 112C1 of the left eye 111L and the corneal reflex center 113C1 of the left eye 111L in the X-axis direction, and calculates the distance Ly between the pupil center 112C1 of the left eye 111L and the corneal reflex center 113C1 of the left eye 111L in the Y-axis direction.

As illustrated in FIG. 18, the position calculating unit 212 calculates the distance D between the corneal reflex center 113Cr of the right eye 111R and the corneal reflex center 113C1 of the left eye 111L when the position of the pupil center 112Cr of the right eye 111R and the position of the pupil center 112C1 of the left eye 111L are set to be coincident in the X-Y plane. That is, the position calculating unit 212 performs the calculation given in Equation (2).

$$D=\sqrt{(Lx-Rx)^2+(Ly-Ry)^2} \qquad (2)$$

Based on the distance D, the evaluating unit 218 outputs the evaluation data about the visual performance of the test subject.

Figure 19:
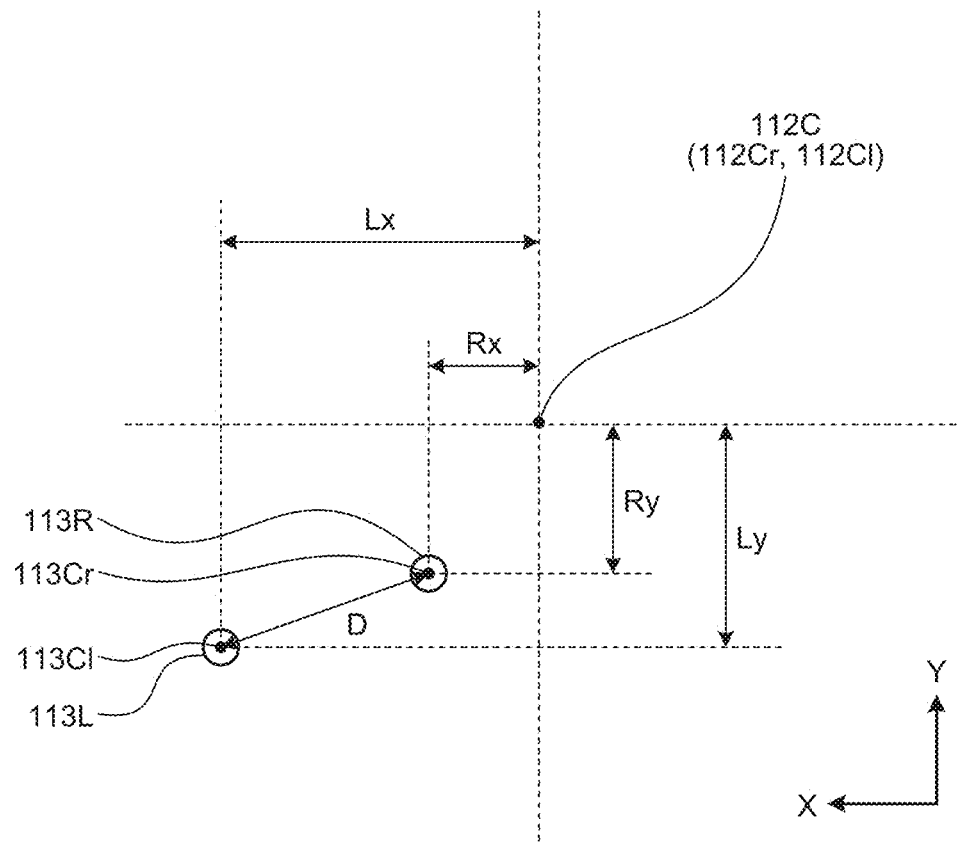
FIG. 19 is a diagram that schematically illustrates the example of the result of performing image processing with respect to the image data of the right eye and the image data of the left eye according to the second embodiment.

FIG. 18 is a diagram that schematically illustrates an example of the image data obtained by synthesizing the image data of the right eye 111R and the image data of the left eye 111L of the test subject who does not have the tendency for strabismus. FIG. 19 is a diagram that schematically illustrates an example of the image data obtained by synthesizing the image data of the right eye 111R and the image data of the left eye 111L of the test subject who has the tendency for strabismus. As illustrated in FIG. 18, when the test subject does not have the tendency for strabismus, the distance D is short. However, as illustrated in FIG. 19, when the test subject has the tendency for strabismus, the distance D is long.

In the second embodiment, if the distance D is equal to or greater than a threshold value SH, then the evaluating unit 218 outputs the evaluation data indicating that there is abnormality in the visual performance of the test subject. That is, if the distance D is equal to or greater than the threshold value SH, then the evaluating unit 218 determines that the test subject has the tendency for strabismus, and outputs the evaluation data indicating that the test subject has the tendency for strabismus.

On the other hand, if the distance D is not equal to or greater than the threshold value SH, then the evaluating unit 218 outputs the evaluation data indicating that the test subject has normal visual performance. That is, if the distance D is smaller than the threshold value SH, then the evaluating unit 218 determines that the test subject does not have the tendency for strabismus, and outputs the evaluation data indicating that the test subject does not have the tendency for strabismus.

Herein, the threshold value SH is derived either statistically or empirically based on the data obtained from a plurality of test subjects who have the tendency for strabismus, and is stored in the memory unit 220. In the second embodiment, the threshold value SH is set to a value in the range from equal to or greater than 5 [%] of the diameter of the pupil 112 to equal to or smaller than 10 [%] of the diameter of the pupil 112. For example, the threshold value SH in the range from equal to or greater than 0.07 [mm] to equal to or smaller than 0.13 [mm].

The output control unit 222 outputs, to the display device 101 or the output device 50, either the evaluation data indicating the tendency for strabismus or the evaluation data indicating no tendency for strabismus.

As explained above, according to the second embodiment, the image data of the right eye 111R and the image data of the left eye 111L are synthesized, and the distance D between the corneal reflex center 113Cr of the right eye 111R and the corneal reflex center 113C1 of the left eye 111L is calculated when the position of the pupil center 112Cr of the right eye 111R and the position of the pupil center 112C1 of the left eye 111L are set to be coincident in the X-Y plane. Then, based on the distance D that is a scalar value, the state of strabismus of the test subject is evaluated. That enables achieving reduction in the load of the arithmetic processing.

In the second embodiment, the indicator 130, on which the test subject is to be made to fix the eyes, may be displayed at the center of the display screen 101S or may be displayed at an end portion of the display screen 101S. The position of the indicator 130 in the display screen 101S has only a small effect on the calculation of the distance D.

Third Embodiment

Given below is the explanation of a third embodiment. In the following explanation, the constituent elements that are identical or equivalent to the embodiments described above are referred to by the same reference numerals, and their explanation is either simplified or omitted.

Figure 20:
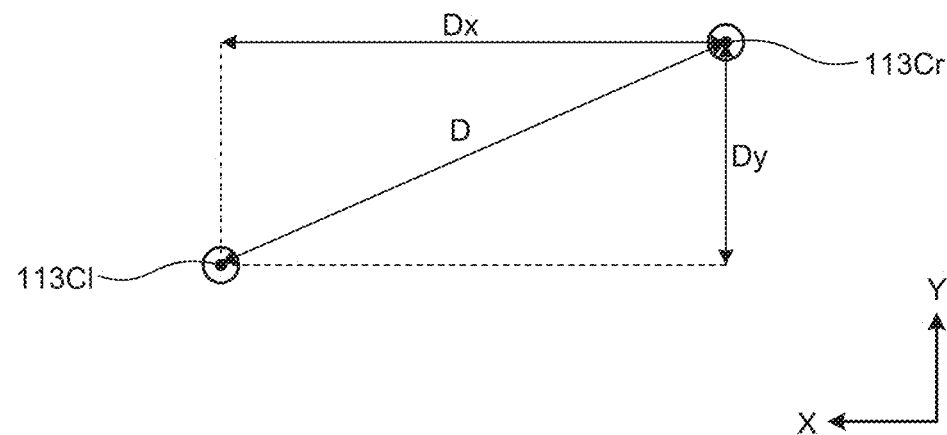
FIG. 20 is a diagram that schematically illustrates an example of the result of image processing performed with respect to the image data of the right eye and the image data of the left eye according to a third embodiment.

FIG. 20 is a diagram that schematically illustrates an example of the result of image processing performed with respect to the image data of the right eye 111R and the image data of the left eye 111L according to the third embodiment. Herein, the third embodiment represents an application example of the second embodiment.

In the third embodiment, as illustrated in FIG. 20, the position calculating unit 212 calculates a distance Dx representing the component in the X-axis direction of the distance D, and calculates a distance Dy representing the component in the Y-axis direction of the distance D. The distance Dx represents the distance between the corneal reflex center 113Cr of the right eye 111R and the corneal reflex center 113C1 of the left eye 111L in the X-axis direction. The distance Dy represents the distance between the corneal reflex center 113Cr of the right eye 111R and the corneal reflex center 113C1 of the left eye 111L in the Y-axis direction.

Based on the distance Dx, the evaluating unit 218 can evaluate whether or not the test subject has the tendency for esotropia or exotropia. Moreover, based on the distance Dy, the evaluating unit 218 can evaluate whether or not the test subject has the tendency for hypertropia or hypotropia.

For example, if the distance Dx is equal to or greater than a predetermined threshold value, then the test subject is evaluated to have the tendency for esotropia or exotropia. Similarly, if the distance Dy is equal to or greater than a predetermined threshold value, then the test subject is evaluated to have the tendency for hypertropia or hypotropia.

Fourth Embodiment

Given below is the explanation of a fourth embodiment. In the following explanation, the constituent elements that are identical or equivalent to the embodiments described above are referred to by the same reference numerals, and their explanation is either simplified or omitted.

In the fourth embodiment, the explanation is given for an example in which the first-type relative position data contains time-series data of the relative positions between the pupil center 112Cr of the right eye 111R and the corneal reflex center 113Cr of the right eye 111R during a specified time period PT; and the second-type relative position data contains time-series data of the relative positions between the pupil center 112C1 of the left eye 111L and the corneal reflex center 113C1 of the left eye 111L during the specified time period PT.

Figure 21:
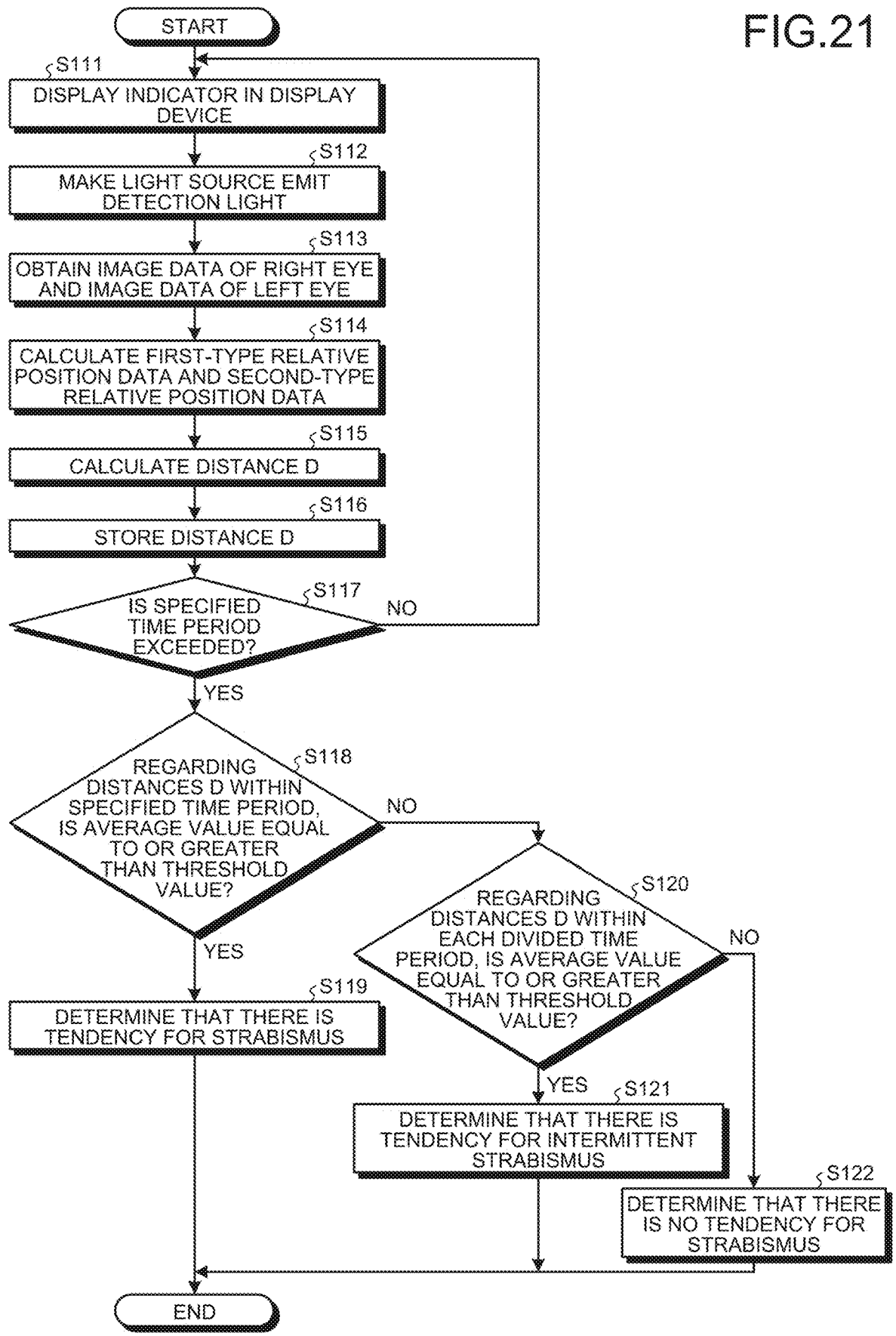
FIG. 21 is a flowchart for explaining an example of a strabismus examination method according to a fourth embodiment.

FIG. 21 is a flowchart for explaining an example of a strabismus examination method according to the fourth embodiment. The display control unit 208 displays the indicator 130, on which the test subject is to be made to fix the eyes, in the display device 101 (Step S111). Herein, the display control unit 208 may display the indicator 130 at the center of the display screen 101S or at an end portion of the display screen 101S. Moreover, the display control unit 208 may display, in the display device 101, the indicator 130 that either remains stationary or moves within the display screen 101S.

In the fourth embodiment, the display control unit 208 displays, in the display device 101, the indicator 130 that remains stationary as well as moves around within the display screen 101S of the display device 101. The test subject is instructed to focus on the indicator 130 displayed in the display device 101.

The detection light is emitted from the light source 103 (Step S112). Then, the image data of the right eye 111R and the image data of the left eye 111L of the test subject, who is irradiated with the detection light, are obtained by the stereo camera device 102.

The image data obtaining unit 202 obtains the image data of the right eye 111R and the image data of the left eye 111L of the test subject, who is irradiated with the detection light, from the stereo camera device 102 (Step S113).

Based on the image data of the right eye 111R, the position calculating unit 212 calculates the position data of the pupil center 112Cr of the right eye 111R and the position data of the corneal reflex center 113Cr of the right eye 111R in the X-Y plane. Moreover, based on the image data of the left eye 111L, the position calculating unit 212 calculates the position data of the pupil center 112C1 of the left eye 111L and the position data of the corneal reflex center 113C1 of the left eye 111L in the X-Y plane.

Then, based on the position data of the pupil center 112Cr of the right eye 111R and the position data of the corneal reflex center 113Cr of the right eye 111R in the X-Y plane, the position calculating unit 212 calculates the first-type relative position data that indicates the relative position between the pupil center 112Cr of the right eye 111R and the corneal reflex center 113Cr of the right eye 111R in the X-Y plane. Moreover, based on the position data of the pupil center 112C1 of the left eye 111L and the position data of the corneal reflex center 113C1 of the left eye 111L in the X-Y plane, the position calculating unit 212 calculates the second-type relative position data that indicates the relative position between the pupil center 112C1 of the left eye 111L and the corneal reflex center 113C1 of the left eye 111L in the X-Y plane (Step S114).

In an identical manner to the embodiments described earlier, the position calculating unit 212 calculates, as the first-type relative position data, the distance Rx between the pupil center 112Cr of the right eye 111R and the corneal reflex center 113Cr of the right eye 111R in the X-axis direction, and the distance Ry between the pupil center 112Cr of the right eye 111R and the corneal reflex center 113Cr of the right eye 111R in the Y-axis direction. Moreover, the position calculating unit 212 calculates, as the second-type relative position data, the distance Lx between the pupil center 112C1 of the left eye 111L and the corneal reflex center 113C1 of the left eye 111L in the X-axis direction, and the distance Ly between the pupil center 112C1 of the left eye 111L and the corneal reflex center 113C1 of the left eye 111L in the Y-axis direction.

Furthermore, in an identical manner to the embodiments described earlier, the image processing unit 206 synthesizes the image data of the right eye 111R and the image data of the left eye 111L in such a way that the position of the pupil center 112Cr of the right eye 111R and the position of the pupil center 112C1 of the left eye 111L become coincident in the X-Y plane. The position calculating unit 212 calculates the distance D between the corneal reflex center 113Cr of the right eye 111R and the corneal reflex center 113C1 of the left eye 111L when the position of the pupil center 112Cr of the right eye 111R and the position of the pupil center 112C1 of the left eye 111L are set to be coincident in the X-Y plane (Step S115).

The distance D calculated at Step S115 is stored in the memory unit 220 (Step S116).

The visual performance examination device 100 performs the operations from Step S111 to Step S116 in specified cycles. In the fourth embodiment, the operations from Step S111 to Step S116 are performed for 50 times in one second. Moreover, the operations from Step S111 to Step S116 are performed for the predetermined specified time period PT. In the fourth embodiment, the specified time period PT is set to 30 seconds. However, the specified time period PT can be set to an arbitrary period of time.

That is, in the fourth embodiment, based on the first-type relative position data and the second-type relative position data within the specified time period PT, the position calculating unit 212 calculates, in specified cycles, time-series data of the distances D between the corneal reflex center 113Cr of the right eye 111R and the corneal reflex center 113C1 of the left eye 111L when the position of the pupil center 112Cr of the right eye 111R and the position of the pupil center 112C1 of the left eye 111L are set to be coincident in the X-Y plane. The calculated time-series data of the distances D is sequentially stored in the memory unit 220.

The evaluating unit 218 determines whether or not the elapsed time since the start of the operations from Step S111 to Step S116 has exceeded the specified time period PT (Step S117).

At Step S117, if it is determined that the elapsed time has not exceeded the specified time period PT (No at Step S117), then the system control returns to Step S111 and the operations from Step S111 to Step S116 are again performed.

On the other hand, at Step S117, if it is determined that the elapsed time has exceeded the specified time period PT (Yes at Step S117); then, based on the data indicating a plurality of distances D stored in the memory unit 220, the evaluating unit 218 calculates the average value of the distances D within the specified time period PT. In the fourth embodiment, the distance D is calculated for 50 times in one second, and the specified time period PT is set to 30 seconds. Hence, in the memory unit 220, data indicating 1500 samples of the distance D is stored. The evaluating unit 218 calculates the average value of the 1500 samples of the distance D.

Subsequently, based on the average value of the distances D within the specified time period PT, the evaluating unit 218 outputs the evaluation data about the visual performance of the test subject. In the fourth embodiment, the evaluating unit 218 determines whether or not the average value of the distances D within the specified time period PT is equal to or greater than a predetermined threshold value SK (Step S118).

At Step S118, if it is determined that the average value of the distances D within the specified time period PT is equal to or greater than the threshold value SK (Yes at Step S118), then the evaluating unit 218 outputs the evaluation data indicating that there is abnormality in the visual performance of the test subject (Step S119). That is, the evaluating unit 218 determines that the test subject has the tendency for strabismus, and outputs the evaluation data indicating that the test subject has the tendency for strabismus.

On the other hand, at Step S118, if it is determined that the average value of the distances D within the specified time period PT is not equal to or greater than the threshold value SK (No at Step S118); then, based on the data indicating a plurality of distances D as stored in the memory unit 220, the evaluating unit 218 calculates the average value of the distances D within each of a plurality of divided time periods DT obtained by dividing the specified time period PT. Thus, the dividing time periods DT are shorter than the specified time period PT. When the specified time period PT is set to 30 seconds, the divided time periods DT are set to, for example, a range from equal to or greater than one second to equal to or smaller than 10 seconds.

Based on the average value of the distances D within each of a plurality of divided time periods DT, the evaluating unit 218 outputs the evaluation data about the visual performance of the test subject. In the fourth embodiment, the evaluating unit 218 determines whether or not the average value of the distances D within each divided time period DT is equal to or greater than the predetermined threshold value SK (Step S120).

At Step S120, if it is determined that the average value of the distances D within each divided time period DT is equal to or greater than the threshold value SK (Yes at Step S120), then the evaluating unit 218 outputs the evaluation data indicating that there is abnormality in the visual performance of the test subject (Step S121). In the fourth embodiment, the evaluating unit 218 determines that the test subject has the tendency for intermittent strabismus, and outputs the evaluation data indicating that the test subject has the tendency for intermittent strabismus.

The intermittent strabismus implies strabismus having two states including the state in which strabismus appears and the state in which no strabismus appears.

On the other hand, at Step S120, if it is determined that the average value of the distances D in each divided time period DT is not equal to or greater than the threshold value SK (No at Step S120), then the evaluating unit 218 outputs the evaluation data indicating that there is no abnormality in the visual performance of the test subject (Step S122). That is, the evaluating unit 218 determines that the test subject does not have the tendency for strabismus, and outputs the evaluation data indicating that the test subject does not have the tendency for strabismus.

Figure 22:
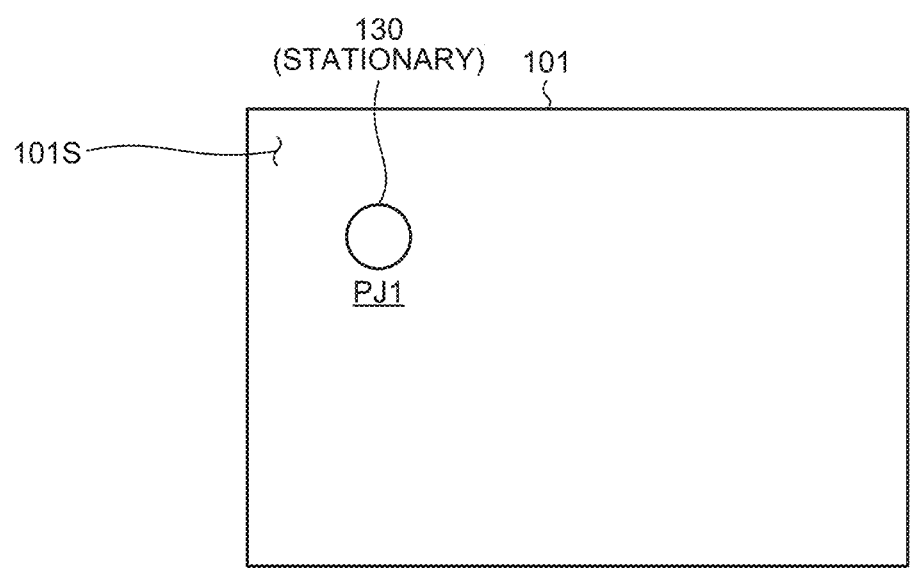
FIG. 22 is a diagram that schematically illustrates the indicator that is displayed in the display device according to the fourth embodiment.
Figure 22:
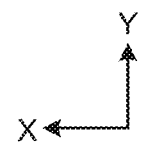
Figure 23:
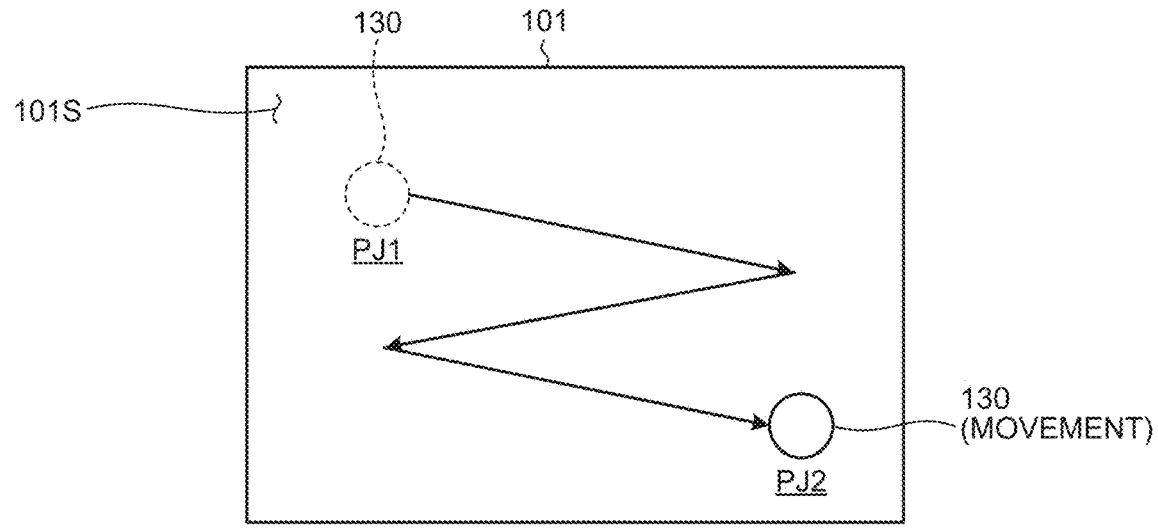
FIG. 23 is a diagram that schematically illustrates the indicator that is displayed in the display device according to the fourth embodiment.
Figure 24:
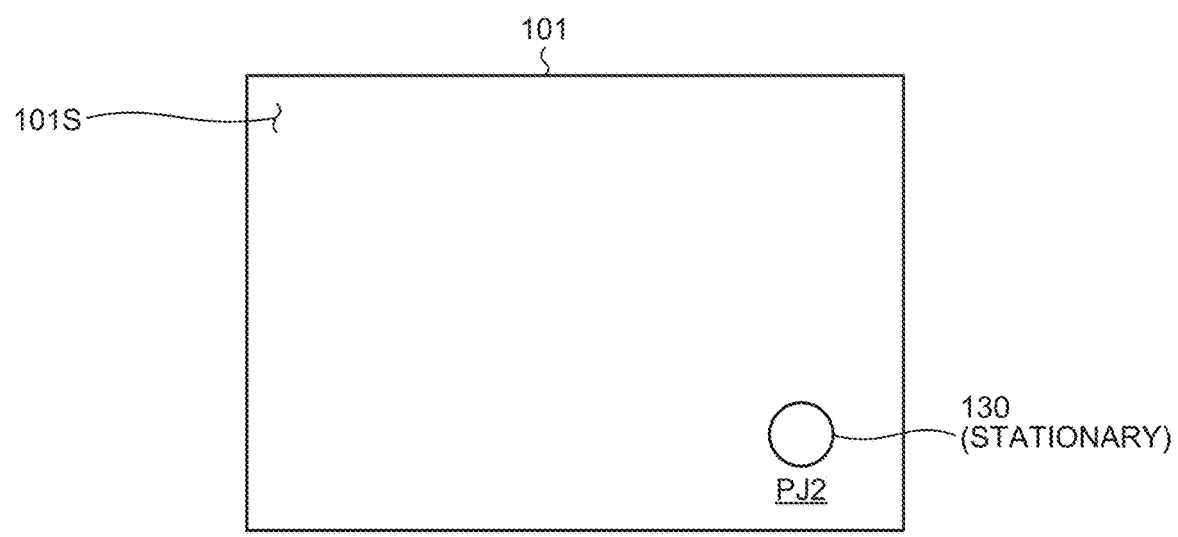
FIG. 24 is a diagram that schematically illustrates the indicator that is displayed in the display device according to the fourth embodiment.

FIGS. 22, 23, and 24 are diagrams that schematically illustrate the indicator 130 that is displayed in the display device 101 according to the fourth embodiment. As described earlier, in the fourth embodiment, the display control unit 208 displays, in the display device 101, the indicator 130 that remains stationary as well as moves around within the display screen 101S of the display device 101.

As illustrated in FIG. 22, the display control unit 208 displays, in the display device 101, the indicator 130 that remains stationary at a first position PJ1 in the display screen 101S of the display device 101. In the fourth embodiment, the first position PJ1 is defined in the end portion present in the +X direction and the +Y direction of the display screen 101S. Meanwhile, the first position PJ1 can be set at an arbitrary position in the display screen 101S.

In the fourth embodiment, the display control unit 208 keeps the indicator 130 stationary for 11 seconds at the first position PJ1 in the display screen 101S.

After keeping the indicator 130 stationary for 11 seconds at the first position PJ1, the display control unit 208 moves the indicator 130 within the display screen 101S. As illustrated in FIG. 23, the display control unit 208 moves the indicator 130 from the first position PJ1 to a second position PJ2 within the display screen 101S. In the fourth embodiment, the second position PJ2 is defined in the end portion present in the −X direction and the −Y direction of the display screen 101S. Meanwhile, the second position PJ2 can be set at an arbitrary position in the display screen 101S.

The movement locus of the indicator 130 from the first position PJ1 to the second position PJ2 can be either linear, or curved, or zigzag having a plurality of bends.

In the fourth embodiment, the display control unit 208 moves the indicator 130 from the first position PJ1 to the second position PJ2 in six seconds.

As illustrated in FIG. 24, the display control unit 208 displays, in the display device 101, the indicator 130 that remains stationary at the second position PJ2 in the display screen 101S of the display device 101.

In the fourth embodiment, the display control unit 208 keeps the indicator 130 stationary for 13 seconds at the second position PJ2 in the display screen 101S.

The divided time periods DT are decided based on the movement condition of the indicator 130 in the display screen 101S. Thus, the divided time periods DT are decided based on the stationary period for which the indicator 130 remains stationary in the display screen 101S. Moreover, the divided time periods DT are decided based on the moving period for which the indicator 130 keeps moving in the display screen 101S.

In the fourth embodiment, based on the stationary period for which the indicator 130 remains stationary at the first position PJ1 in the display screen 101S, a first divided time period DT1 is decided. Moreover, based on the moving period for which the indicator 130 keeps moving from the first position PJ1 to the second position PJ2 in the display screen 101S, a second divided period DT2 is decided. Furthermore, based on the stationary period for which the indicator 130 remains stationary at the second position PJ2 in the display screen 101S, a third divided time period DT3 is decided.

Figure 25:
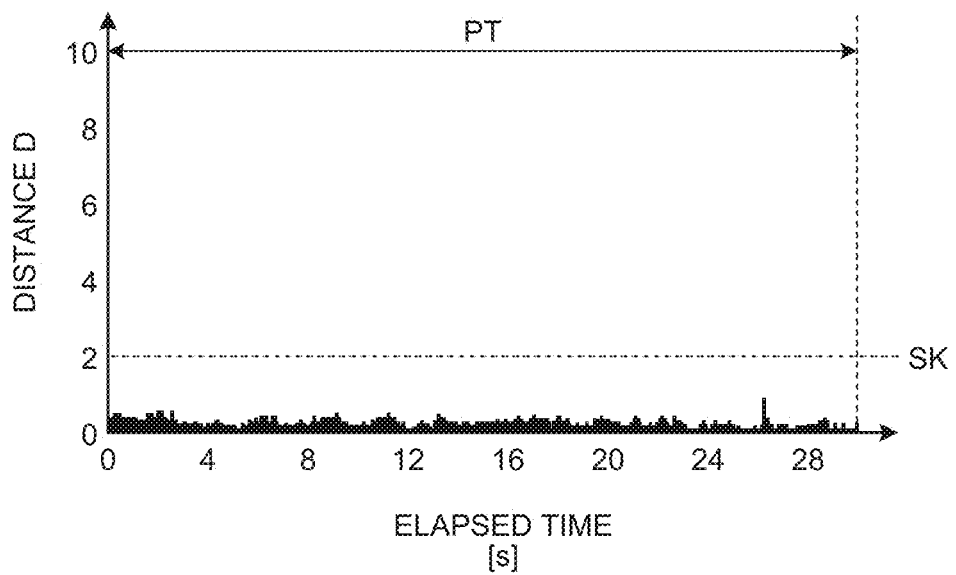
FIG. 25 is a diagram that schematically illustrates an example of time-series data of distances as stored in a memory unit according to the fourth embodiment.
Figure 26:
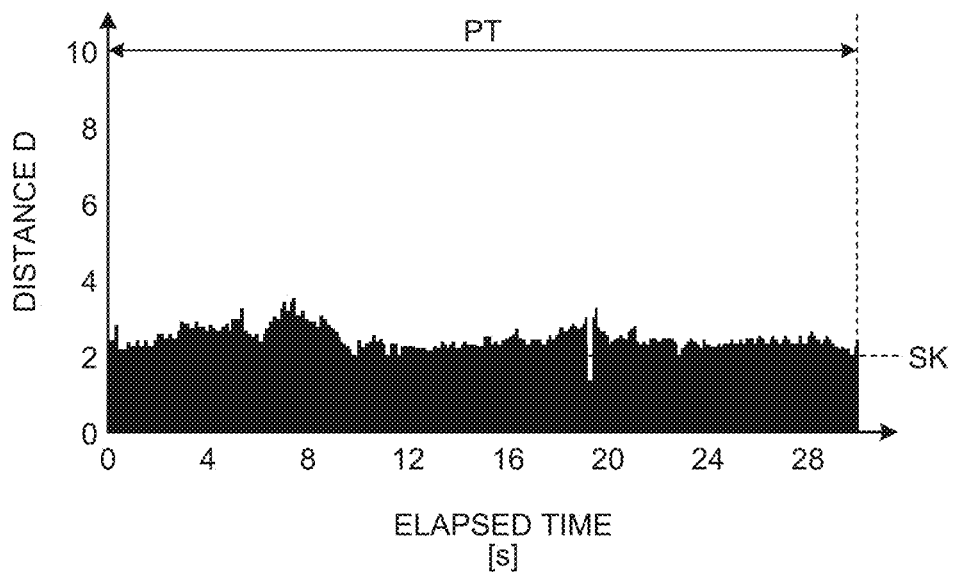
FIG. 26 is a diagram that schematically illustrates the example of time-series data of distances as stored in the memory unit according to the fourth embodiment.
Figure 27:
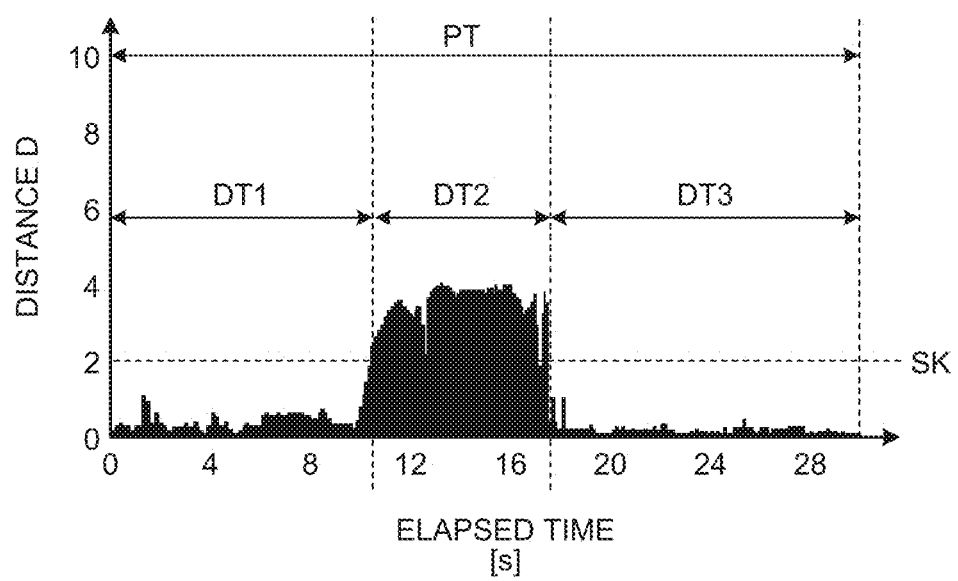
FIG. 27 is a diagram that schematically illustrates the example of time-series data of distances as stored in the memory unit according to the fourth embodiment.

FIGS. 25, 26, and 27 are diagrams that schematically illustrate an example of the time-series data of the distances D as stored in the memory unit 220 according to the fourth embodiment.

As illustrated in FIG. 25, if the distances D are smaller than the threshold value SK over the entire period of the specified time period PT, then it is more likely that the test subject does not have the tendency for strabismus. When the distances D are smaller than the threshold value SK over the entire period of the specified time period PT, the average value of the distances D in the specified time period DT becomes smaller than the threshold value SK. When the time-series data of the distances D is obtained as illustrated in FIG. 25; as explained at Step S112, based on the average value of the distances D in the specified time period PT, the evaluating unit 218 outputs the evaluation data indicating that the test subject does not have the tendency for strabismus.

As illustrated in FIG. 26, if the distances D are equal to or greater than the threshold value SK over the entire period of the specified time period PT, then it is more likely that the test subject has the tendency for strabismus. When the distances D are equal to or greater than the threshold value SK over the entire period of the specified time period PT, the average value of the distances D in the specified time period PT becomes equal to or greater than the threshold value SK. When the time-series data of the distances D is obtained as illustrated in FIG. 26; as explained at Step S119, based on the average value of the distances D in the specified time period PT, the evaluating unit 218 outputs the evaluation data indicating that the test subject has the tendency for strabismus.

As illustrated in FIG. 27, if the distances D become equal to or greater than the threshold value SK in some part of the specified time period PT and if the distances D become smaller than the threshold value SK in some part of the specified time period PT, then it is more likely that the test subject has the tendency for intermittent strabismus. When the distances D become equal to or greater than the threshold value SK in some part of the specified time period PT and when the distances D become smaller than the threshold value SK in some part of the specified time period PT, it is likely that that the average value of the distances D in the specified time period PT becomes smaller than the threshold value SK. That is, when the distances D become equal to or greater than the threshold value SK in some part of the specified time period PT and when the distances D become smaller than the threshold value SK in some part of the specified time period PT; regardless of the fact that the test subject has the tendency for intermittent strabismus, it is likely that the average value of the distances D in the specified time period PT becomes smaller than the threshold value SK. If the average value of the distances D in the specified time period PT becomes smaller than the threshold value SK; then, regardless of the fact that the test subject has the tendency for intermittent strabismus, the evaluating unit 218 may unexpectedly output erroneous evaluation data indicating that the test subject does not have the tendency for strabismus.

In the fourth embodiment, as explained at Steps S118 and S120, if it is determined that the average value of the distances D in the specified time period PT is not equal to or greater than the threshold value SK, then the evaluating unit 218 calculates the average value of the distances D in each of a plurality of divided time periods DT obtained by dividing the specified time period PT. In the fourth embodiment, as illustrated in FIG. 27, the specified time period PT is divided into the first divided time period DT1, the second divided time period DT2, and the third divided time period DT3. As a result of calculating the average value of the distances D in each of a plurality of divided time periods DT, the evaluating unit 218 becomes able to determine whether or not the specified time period DT includes any period of time in which the distances D are equal to or greater than the threshold value SK. With that, when the average value of the distances D in the specified time period PT is smaller than the threshold value SK, if the test subject has the tendency for intermittent strabismus, erroneous evaluation data indicating that the test subject does not have the tendency for strabismus is prevented from being output.

As described above, in the fourth embodiment, the divided time periods DT including the first divided time period DT1, the second divided time period DT2, and the third divided time period DT3 are decided based on the movement condition of the indicator 130 in the display screen 101S. In the fourth embodiment, the first divided time period DT1 is set as the stationary period (in the fourth embodiment, 11 seconds) for which the indicator 130 remains stationary at the first position PJ1 in the display screen 101S. The second divided time period DT2 is set as the moving period (in the fourth embodiment, six seconds) for which the indicator 130 moves from the first position PJ1 to the second position PJ2 in the display screen 101S. The third divided time period DT3 is set as the stationary period (in the fourth embodiment, 13 seconds) for which the indicator 130 remains stationary at the second position PJ2 in the display screen 101S.

Based on the image data of the right eye 111R and the image data of the left eye 111L obtained when the indicator 130, which remains stationary as well as moves around within the display screen 101S, is shown to the test subject; the position calculating unit 212 calculates the time-series data of the distances D in the specified time period PT. Then, based on the time-series data of the distances D obtained when the indicator 130, which remains stationary as well as moves around within the display screen 101S, is shown to the test subject; the evaluating unit 218 outputs the evaluation data about the visual performance of the test subject. In the fourth embodiment, the evaluating unit 218 outputs the evaluation data that indicates the relationship between the state of movement of the eye gaze of the test subject when the indicator 130, which remains stationary as well as moves around within the display screen 101S, is shown to the test subject, and the state of strabismus of the test subject.

If the indicator 130, which remains stationary in the display screen 101S, is shown to the test subject who has the tendency for intermittent strabismus; then it is likely that intermittent strabismus does not appear. On the other hand, if the indicator 130, which moves around within the display screen 101S, is shown to the test subject who has the tendency for intermittent strabismus; then it is more likely that intermittent strabismus appears prominently.

In the fourth embodiment, the second divided time period DT2 is set at the moving period for which the indicator 130 moves around within the display screen 101S. Thus, as a result of calculating the average value of the distance D in the second divided time period DT2, it becomes possible to accurately examine whether or not the test subject has the tendency for intermittent strabismus.

As explained above, according to the fourth embodiment, based on the variation in the distances D in the specified time period PT, the evaluating unit 218 outputs the evaluation data about the visual performance of the test subject. As illustrated in FIG. 25, when there is only a small variation in the distances D in the specified time period PT and when the average value of the distances D in the specified time period PT is smaller than the threshold value SK, the evaluating unit 218 can output the evaluation data indicating that the test subject does not have the tendency for strabismus. As illustrated in FIG. 26, when there is only a small variation in the distances D in the specified time period PT but when the average value of the distances D in the specified time period PT is greater than the threshold value SK, the evaluating unit 218 can output the evaluation data indicating that the test subject has the tendency for strabismus. As illustrated in FIG. 27, when there is a large variation in the distances D in the specified time period PT, the evaluating unit 218 can output the evaluation data indicating that the test subject has the tendency for intermittent strabismus.

Meanwhile, in the fourth embodiment, the evaluation data is output based on the average value of the distances D. However, instead of using the average value of the distances D, it is possible to use some other statistical value (representative value) such as the median value, or the mode value, or the quartile that is representative of a plurality of distances D.

In the fourth embodiment, it is also possible to calculate the time-series data of the differences $\Delta x$ between the distances Rx and the distances Lx in the specified time period PT, and to calculate the time-series data of the differences $\Delta y$ between the distances Ry and the distances Ly in the specified time period PT. Then, based on at least either the variation in the differences $\Delta x$ in the specified time period PT or the variation in the differences $\Delta y$ in the specified time period PT, the evaluating unit 218 can output the evaluation data about the visual performance of the test subject. That is, in the fourth embodiment, based on at least either the variation in the relative positions between the pupil center 112Cr of the right eye 111R and the corneal reflex center 113Cr of the right eye 111R in the specified time period PT or the variation in the relative positions between the pupil center 112Cl of the left eye 111L and the corneal reflex center 113Cl of the left eye 111L in the specified time period PT, the evaluating unit 218 can output the evaluation data about the visual performance of the test subject.

Fifth Embodiment

Given below is the explanation of a fifth embodiment. In the following explanation, the constituent elements that are identical or equivalent to the embodiments described above are referred to by the same reference numerals, and their explanation is either simplified or omitted.

In the fourth embodiment described above, the divided time periods DT are decided based on the movement condition of the indicator 130 in the display screen 101S. Alternatively, the divided time periods DT may be decided in an arbitrary manner without using the movement condition of the indicator 130 as the basis. The divided time periods DT may be decided based on the variation of the distances D in the obtained time-series data of the distances D.

Figure 28:
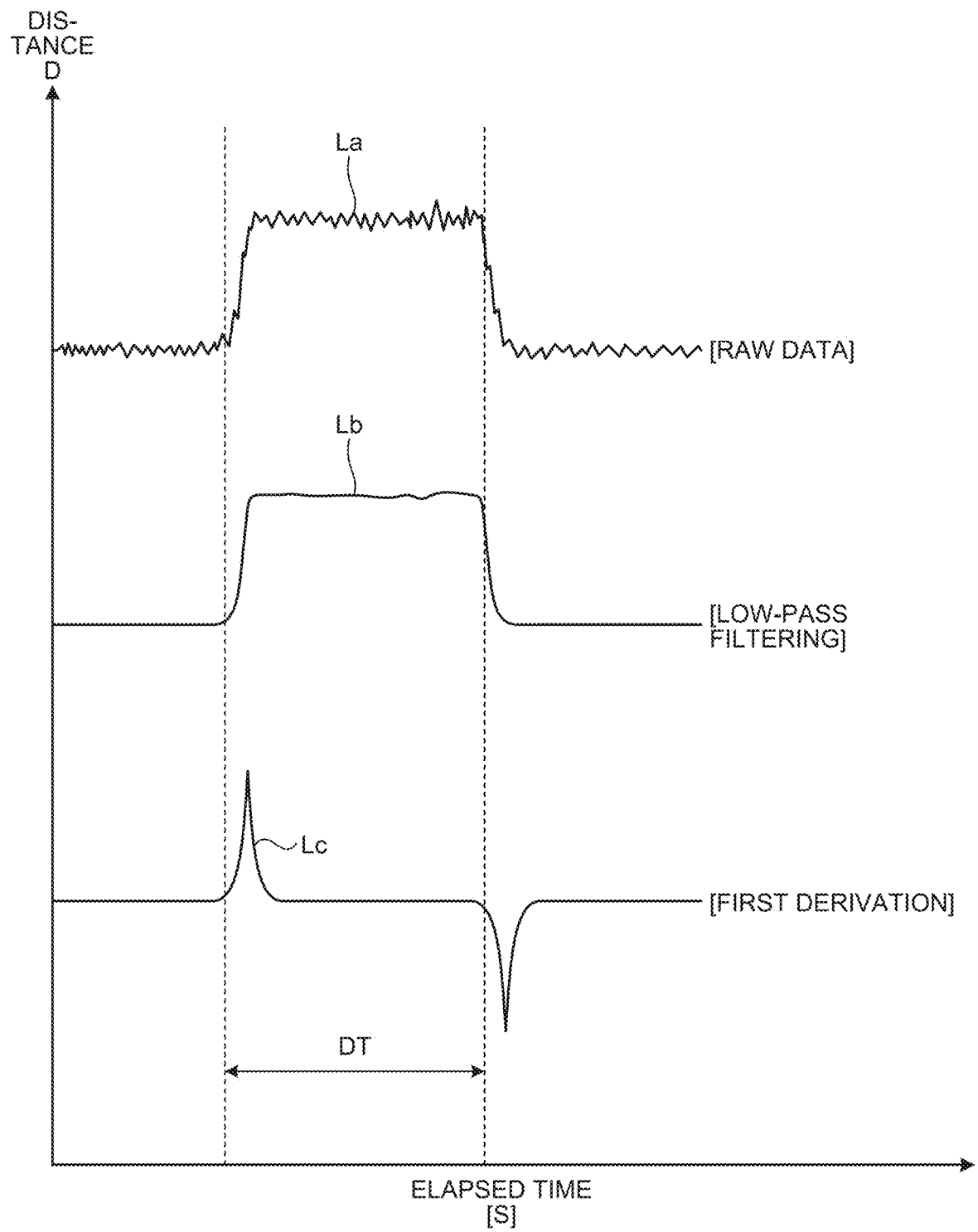
FIG. 28 is a diagram that schematically illustrates an exemplary method of deciding on divided time periods according to a fifth embodiment.

FIG. 28 is a diagram that schematically illustrates an exemplary method of deciding on the divided time periods DT according to the fifth embodiment. When the time-series data of the distances D (raw data) is obtained as illustrated by a line La in FIG. 28; for example, the image processing unit 206 performs low-pass filtering with respect to the time-series data of the distances D. As a result, as illustrated by a line Lb in FIG. 28, time-series data of the distances D is generated with a reduced effect of noise. Herein, it is desirable that the time constant in low-pass filtering is decided based on the second divided time period DT2.

Moreover, the image processing unit 206 performs the first derivation of the time-series data of the distances D indicated by the line Lb, and extracts first derivative values as illustrated by a line Lc in FIG. 28. As a result, the points of time at which the distance D drastically varies are extracted. Then, the interval between a point of time at which the distance D drastically increases and a point of time at which the distance D drastically decreases is decided as a divided time period DT.

Sixth Embodiment

Given below is the explanation of a sixth embodiment. In the following explanation, the constituent elements that are identical or equivalent to the embodiments described above are referred to by the same reference numerals, and their explanation is either simplified or omitted.

In the sixth embodiment, the explanation is given about an example in which the indicators 130 are displayed at each of a plurality of positions in the display screen 101S of the display device 101; the position data of the corneal reflexes 113 is calculated based on the image data of the eyes 111 of the test subject that is obtained when each of a plurality of indicators 130 is shown to the test subject; and the evaluation data about the visual performance of the test subject is output based on the relative positions of the indicators 130 and the relative positions of the corneal reflexes 113.

Figure 29:
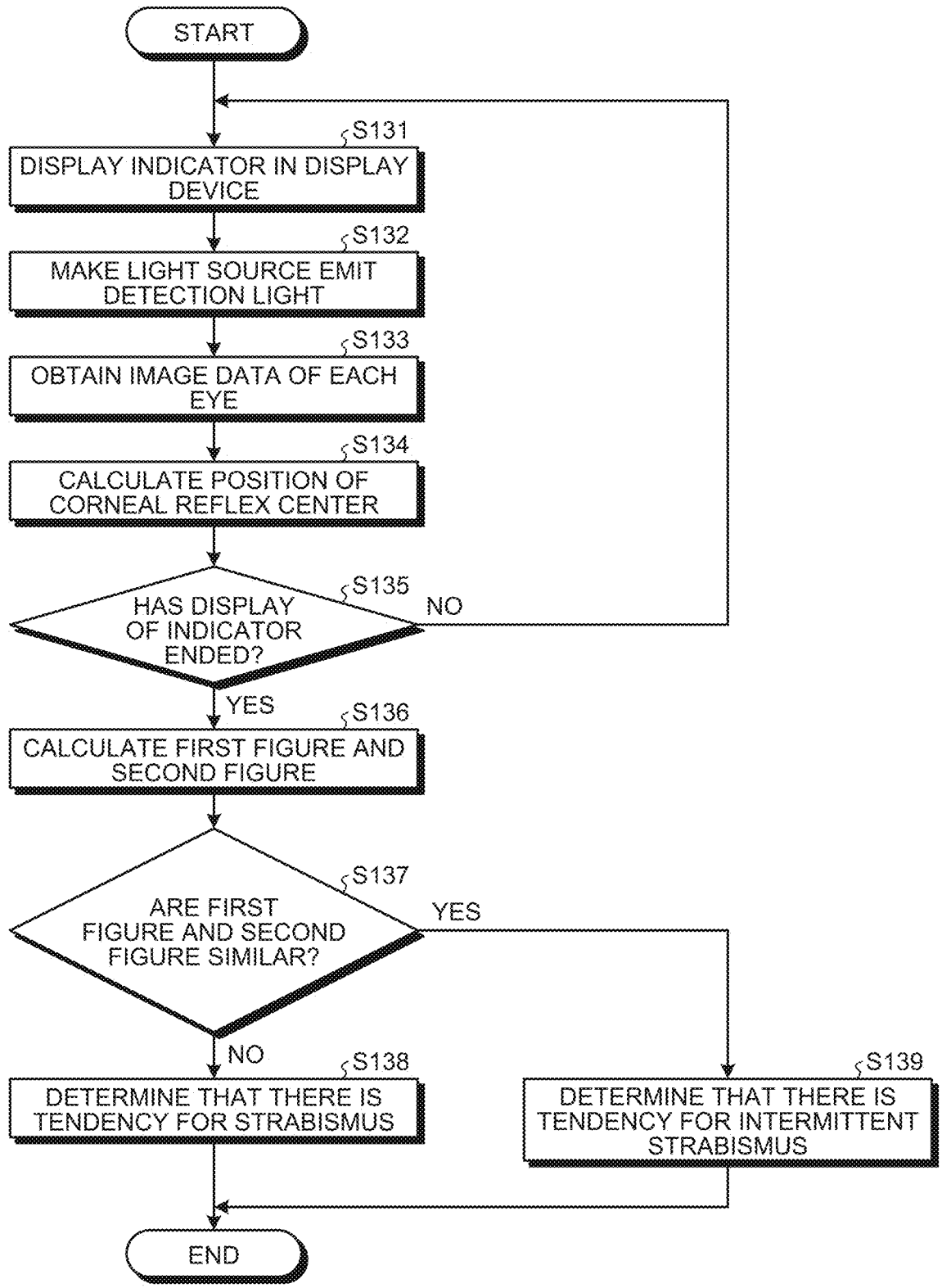
FIG. 29 is a flowchart for explaining an example of a strabismus examination method according to a sixth embodiment.

FIG. 29 is a flowchart for explaining an example of a strabismus examination method according to the sixth embodiment. The display control unit 208 displays the indicators 130, on which the test subject is to be made to fix the eyes, in the display device 101 (Step S131).

In the sixth embodiment, the display control unit 208 displays the indicators 130 at each of a plurality of positions in the display screen 101S of the display device 101. The test subject is instructed to focus on the indicators 130 displayed in the display device 101.

The detection light is emitted from the light source 103 (Step S132). Then, the image data of the right eye 111R and the image data of the left eye 111L of the test subject, who is irradiated with the detection light, are obtained by the stereo camera device 102.

The image data obtaining unit 202 obtains the image data of the right eye 111R and the image data of the left eye 111L of the test subject, who is irradiated with the detection light, from the stereo camera device 102 (Step S133).

Based on the image data of the right eye 111R, the position calculating unit 212 calculates the position data of the corneal reflex center 113Cr of the right eye 111R in the X-Y plane when the indicators 130 displayed in the display screen 101S are shown. Moreover, based on the image data of the left eye 111L, the position calculating unit 212 calculates the position data of the corneal reflex center 113Cl of the left eye 111L in the X-Y plane when the indicators 130 displayed in the display screen 101S are shown (Step S134).

The visual performance examination device 100 performs the operations from Step S131 to Step S134 in specified cycles. The operations from Step S131 to Step S134 are performed until the indicators 130 are no more displayed at each of a plurality of positions in the display screen 101S.

That is, in the sixth embodiment, based on the image data of the right eye 111R, the position calculating unit 212 calculates the position data of the corneal reflex center 113Cr of the right eye 111R in the X-Y plane when the indicator 130 displayed at each of a plurality of positions in the display screen 101S is shown. Moreover, based on the image data of the left eye 111L, the position calculating unit 212 calculates the position data of the corneal reflex center 113Cl of the left eye 111L in the X-Y plane when the indicator 130 displayed at each of a plurality of positions in the display screen 101S is shown.

The evaluating unit 218 determines whether or not the display of the indicator 130 at each of a plurality of positions in the display screen 101S has ended (Step S135).

At Step S135, if it is determined that the display of the indicators 130 has not ended (No at Step S135), then the system control returns to Step S131 and the operations from Step S131 to Step S134 are again performed.

On the other hand, at Step S135, when it is determined that the display of the indicators 130 has ended (Yes at Step S135), the evaluating unit 218 calculates a first figure CA1 that is defined according to the relative positions of the indicators 130 and calculates a second figure CA2 that is defined according to the relative positions of the corneal reflex centers 113C (Step S136), respectively.

Figure 30:
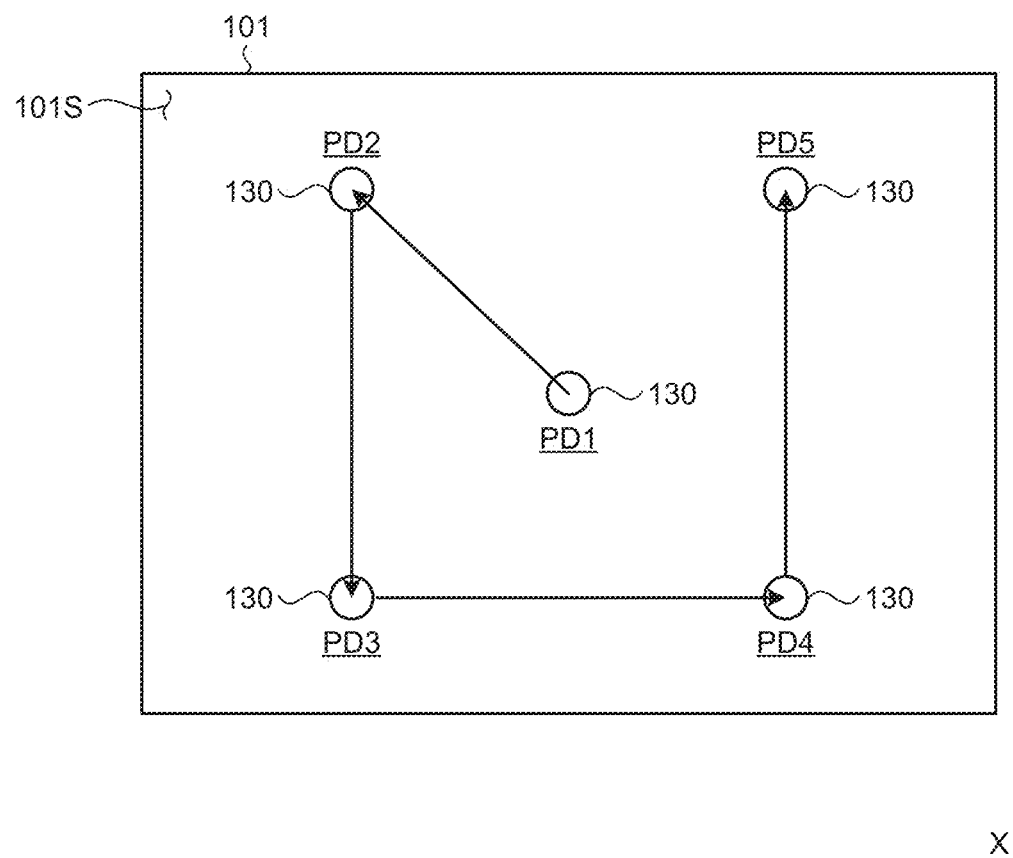
FIG. 30 is a diagram that schematically illustrates an example of the indicators displayed in the display device according to the sixth embodiment.

FIG. 30 is a diagram that schematically illustrates an example of the indicators 130 displayed in the display device 101 according to the sixth embodiment. As illustrated in FIG. 30, the display control unit 208 displays the indicators 130 at each of a plurality of positions PD1, PD2, PD3, PD4, and PD5 in the display screen 101S of the display device 101. In the sixth embodiment, the display device 101 sequentially displays the indicator 130 at each of the position PD1, the position PD2, the position PD3, the position PD4, and the position PD5 in the display screen 101S.

The indicator 130 displayed at the position PD2 and the indicator 130 displayed at the position PD3 are neighboring each other. Moreover, the indicator 130 displayed at the position PD3 and the indicator 130 displayed at the position PD4 are neighboring each other. Furthermore, the indicator 130 displayed at the position PD4 and the indicator 130 displayed at the position PD5 are neighboring each other. Moreover, the indicator 130 displayed at the position PD5 and the indicator 130 displayed at the position PD2 are neighboring each other.

In the sixth embodiment, according to the relative positions of the indicator 130 displayed at the position PD2, the indicator 130 displayed at the position PD3, the indicator 130 displayed at the position PD4, and the indicator 130 displayed at the position PD5; a square shape is defined as the first figure CA1. Thus, a distance Va between the position PD2 and the position PD3, a distance Vb between the position PD3 and the position PD4, a distance Vc between the position PD4 and the position PD5, and a distance Vd between the position PD5 and the position PD2 are all identical to each other.

In the sixth embodiment, the display control unit 208 displays the indicator 130 at the position PD1; moves the indicator 130 from the position PD1 to the position PD2; moves the indicator 130 from the position PD2 to the position PD3; moves the indicator 130 from the position PD3 to the position PD4; and moves the indicator 130 from the position PD4 to the position PD5. That is, in the sixth embodiment, the display control unit 208 displays the indicator 130 in the display screen 101S in such a way that the indicator 130 moves from the position PD1 to the position PD5 via the positions PD2, PD3, and PD4 in that order.

In the sixth embodiment, the display control unit 208 displays the indicator 130 in the display device 101 in such a way that the indicator 130 remains stationary as well as moves around within the display screen 101S. In the sixth embodiment, the display control unit 208 keeps the indicator 130 stationary for two seconds at the position PD1, and then moves the indicator 130 from the position PD1 to the position PD2 in one second. In an identical manner, the display control unit 208 keeps the indicator 130 stationary for two seconds at each of the positions PD2, PD3, and PD4; and moves the indicator 130 from the position PD2 to the position PD3 in one second, moves the indicator 130 from the position PD3 to the position PD4 in one second, and moves the indicator 130 from the position PD4 to the position PD5 in one second. Subsequently, the display control unit 208 keeps the indicator 130 stationary for two seconds at the position PD5, and then ends the display of the indicator 130.

In the sixth embodiment, since the time when the indicator 130 starts moving from the position PD1 till the time when the indicator 130 reaches the position PD5 via the positions PD2, PD3 and PD4; the indicator 130 is continuously displayed in the display device 101. Alternatively, the indicator 130 may be displayed in an intermittent manner in the display device 101. For example, in at least some part of the movement section from the position PD1 to the position PD2, in at least some part of the movement section from the position PD2 to the position PD3, in at least some part of the movement section from the position PD3 to the position PD4, and in at least some part of the movement section from the position PD4 to the position PD5; the indicator 130 may not be displayed in the display device 101. Still alternatively, the indicator 130 may be sequentially displayed only at each of the positions PD1, PD2, PD3, PD4, and PD5 in the display screen 101S.

Figure 31:
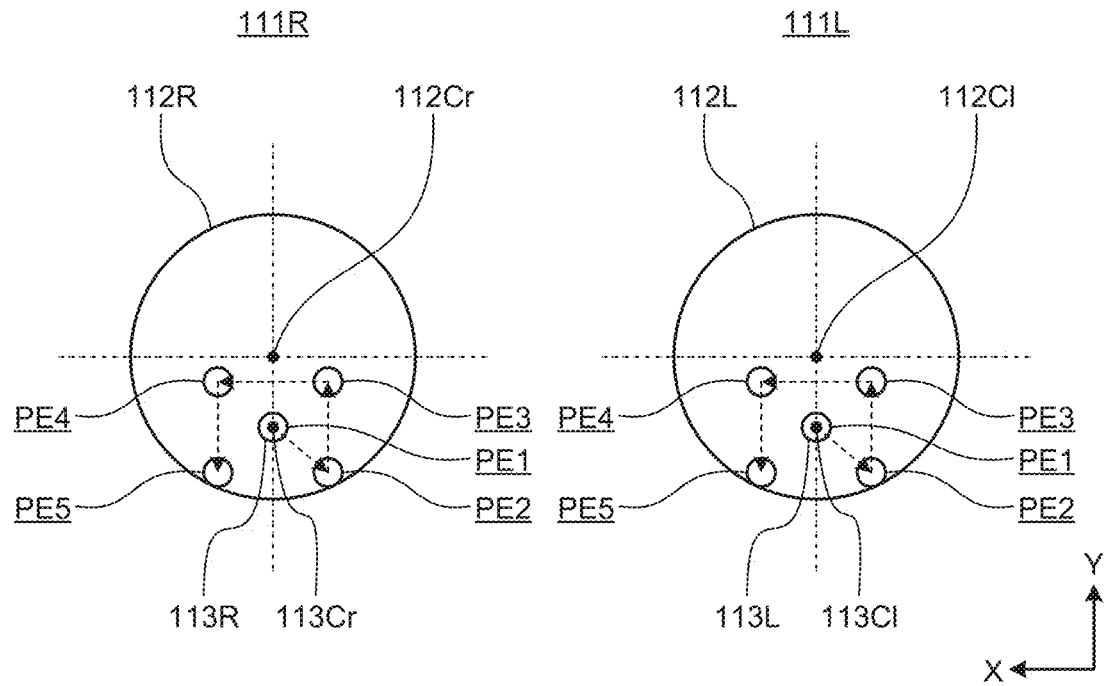
FIG. 31 is a diagram that schematically illustrates an example of the image data of the eyes of a test subject who does not have the tendency for strabismus.

FIG. 31 is a diagram that schematically illustrates an example of the image data obtained by the image data obtaining unit 202 according to the sixth embodiment. FIG. 31 schematically illustrates the image data of the corneal reflexes 113 when the indicator 130 displayed at each of the positions PD1, PD2, PD3, PD4, and PD5 in the display screen 101S is shown to the test subject.

Based on the image data of the right eye 111R, the position calculating unit 212 calculates the position data of the corneal reflex center 113Cr of the right eye 111R in the X-Y plane when the indicator 130 displayed at each of the positions PD1, PD2, PD3, PD4, and PD5 in the display screen 101S is shown to the test subject. Moreover, based on the image data of the left eye 111L, the position calculating unit 212 calculates the position data of the corneal reflex center 113Cl of the left eye 111L in the X-Y plane when the indicator 130 displayed at each of the positions PD1, PD2, PD3, PD4, and PD5 in the display screen 101S is shown to the test subject.

As illustrated in FIG. 31, when the test subject looks at the indicator 130 displayed at the position PD1 in the display screen 101S, each corneal reflex 113 is formed at a position PE1. When the test subject looks at the indicator 130 displayed at the position PD2 in the display screen 101S, each corneal reflex 113 is formed at a position PE2. When the test subject looks at the indicator 130 displayed at the position PD3 in the display screen 101S, each corneal reflex 113 is formed at a position PE3. When the test subject looks at the indicator 130 displayed at the position PD4 in the display screen 101S, each corneal reflex 113 is formed at a position PE4. When the test subject looks at the indicator 130 displayed at the position PD5 in the display screen 101S, each corneal reflex 113 is formed at a position PE5.

The corneal reflex 113 formed at the position PE2 and the corneal reflex 113 formed at the position PE3 are neighboring each other. The corneal reflex 113 formed at the position PE3 and the corneal reflex 113 formed at the position PE4 are neighboring each other. The corneal reflex 113 formed at the position PE4 and the corneal reflex 113 formed at the position PE5 are neighboring each other. The corneal reflex 113 formed at the position PE5 and the corneal reflex 113 formed at the position PE2 are neighboring each other.

In the sixth embodiment, according to the relative positions of the corneal reflex center 113C formed at the position PE2, the corneal reflex center 113C formed at the position PE3, the corneal reflex center 113C formed at the position PE4, and the corneal reflex center 113C formed at the position PE5; a quadrilateral is defined as the second figure CA2. The position PE2 and the position PE3 are separated by a distance Wa. The position PE3 and the position PE4 are separated by a distance Wb. The position PE4 and the position PE5 are separated by a distance Wc. The position PE5 and the position PE2 are separated by a distance Wd.

The evaluating unit 218 determines whether or not the first figure CA1 and the second figure CA2 are similar to each other (Step S137).

In the sixth embodiment, the evaluating unit 218 compares the distance between the neighboring corneal reflexes 113 with a threshold value SQ, and determines the degree of similarity between the first figure CA1 and the second figure CA2. In the sixth embodiment, the evaluating unit 218 determines whether or not Equation (3A) and Equation (3B) hold true.

$$|Wa-Wc|<SQ \quad (3A)$$

$$|Wb-Wd|<SQ \quad (3B)$$

Figure 32:
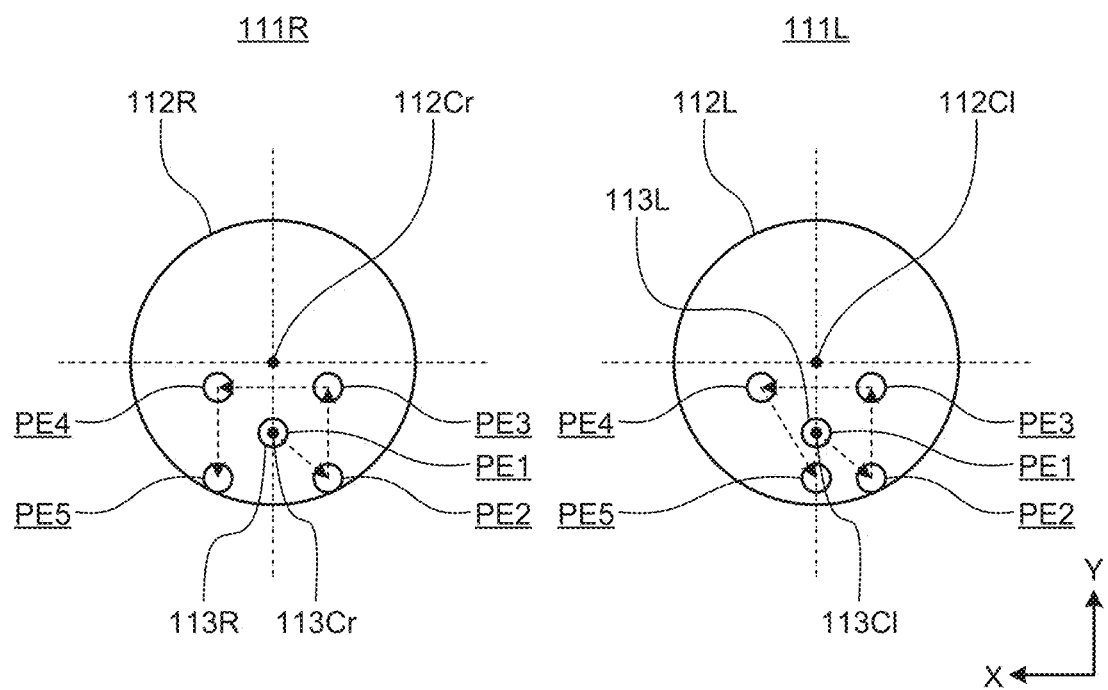
FIG. 32 is a diagram that schematically illustrates an example of the image data of the eyes of a test subject who has the tendency for strabismus.

FIG. 31 is a diagram that schematically illustrates an example of the image data of the eyes 111 of a test subject who does not have the tendency for strabismus. FIG. 32 is a diagram that schematically illustrates an example of the image data of the eyes 111 of a test subject who has the tendency for strabismus in the left eye 111L.

As illustrated in FIG. 31, when the test subject does not have the tendency for strabismus, the second figure CA2 that is defined by the corneal reflex center 113C formed at the position PE2, the corneal reflex center 113C formed at the position PE3, the corneal reflex center 113C formed at the position PE4, and the corneal reflex center 113C formed at the position PE5 essentially has a square shape. That is, when the test subject does not have the tendency for strabismus, the first figure CA1 and the second figure CA2 become similar to each other. In that case, Equation (3A) and Equation (3B) hold true.

On the other hand, as illustrated in FIG. 32, when the left eye 111L of the test subject has the tendency for strabismus, the second figure CA2 that is defined by the corneal reflex center 113C formed at the position PE2, the corneal reflex center 113C formed at the position PE3, the corneal reflex center 113C formed at the position PE4, and the corneal reflex center 113C formed at the position PE5 does not have a square shape. That is, when the test subject has the tendency for strabismus, the first figure CA1 and the second figure CA2 are not similar to each other. In that case, at least either Equation (3A) or Equation (3B) does not hold true.

In this way, in the sixth embodiment, when Equation (3A) and Equation (3B) hold true, the evaluating unit 218 determines that the first figure CA1 and the second figure CA2 are similar to each other. When at least either Equation (3A) or Equation (3B) does not hold true, the evaluating unit 218 determines that the first figure CA1 and the second figure CA2 are not similar to each other.

At Step S137, if it is determined that the first figure CA1 and the second figure CA2 are not similar to each other (No at Step S137), then the evaluating unit 218 outputs the evaluation data indicating that there is abnormality in the visual performance of the test subject (Step S138). That is, when at least either Equation (3A) or Equation (3B) does not hold true, the evaluating unit 218 determines that the test subject has the tendency for strabismus, and outputs the evaluation data indicating that the test subject has the tendency for strabismus.

On the other hand, at Step S137, when it is determined that the first figure CA1 and the second figure CA2 are similar to each other (Yes at Step S137), the evaluating unit 218 outputs the evaluation data indicating the evaluation data indicating that there is no abnormality in the visual performance of the test subject (Step S139). That is, when Equation (3A) and Equation (3B) hold true, the evaluating unit 218 determines that the test subject does not have the tendency for strabismus, and outputs the evaluation data indicating that the test subject does not have the tendency for strabismus.

Meanwhile, the threshold value SQ is derived either statistically or empirically based on the data obtained from a plurality of test subjects who have the tendency for strabismus, and is stored in the memory unit 220.

In the sixth embodiment, the first figure CA1 is compared with the second figure CA2 regarding the right eye 111R. Moreover, the first figure CA1 is compared with the second figure CA2 regarding the left eye 111L. Thus, in the sixth embodiment, whether or not the right eye 111R has the tendency for strabismus can be evaluated, as well as whether or not the left eye 111L has the tendency for strabismus can be evaluated, respectively.

The output control unit 222 outputs, to the display device 101 or the output device 50, either the evaluation data indicating that there is a tendency for strabismus or the evaluation data indicating that there is no tendency for strabismus.

That marks the end of the strabismus examination operation.

As explained above, according to the sixth embodiment, based on the relative positions of a plurality of indicators 130 and based on the relative positions of a plurality of corneal reflexes 113 obtained when the indicators are shown, the evaluation data about the visual performance of the test subject is output. In the sixth embodiment too, in the strabismus examination, it becomes possible to hold down a decline in the examination accuracy even if there is variation in the relative position between the light source 103 and the test subject.

Moreover, according to the sixth embodiment, the evaluation data is output based on the degree of similarity between the first figure CA1, which is defined according to the relative positions of a plurality of indicators 130, and the second figure CA2, which is defined according to the relative positions of a plurality of corneal reflexes 113. That enables achieving reduction in the load of the arithmetic processing performed during the strabismus examination, and enables achieving enhancement in the examination accuracy.

Furthermore, in the sixth embodiment, the first figure CA1 is compared with the second figure CA2 regarding the right eye 111R. Moreover, the first figure CA1 is compared with the second figure CA2 regarding the left eye 111L. Thus, in the sixth embodiment, whether there is a tendency for strabismus in the right eye 111R or in the left eye 111L can be examined in an accurate manner.

Moreover, since it is possible to accurately examine whether there is a tendency for strabismus in the right eye 111R or in the left eye 111L, it becomes possible to hold down a decline in the examination accuracy of the eye gaze detection operation (Step S300). For example, in the strabismus examination operation (Step S100) according to the sixth embodiment, when it is determined that the left eye 111L has the tendency for strabismus but the right eye 111R does not have the tendency for strabismus; in the eye gaze detection operation (Step S300), the eye gaze detection operation is performed with respect to the right eye 111R, so that it becomes possible to hold down a decline in the examination accuracy of the eye gaze detection operation.

Seventh Embodiment

Given below is the explanation of a seventh embodiment. In the following explanation, the constituent elements that are identical or equivalent to the embodiments described above are referred to by the same reference numerals, and their explanation is either simplified or omitted.

The seventh embodiment represents an application example of the sixth embodiment. FIGS. 33, 34, 35, and 36 each are diagrams illustrating an example of the image data of the eyes 111 of the test subject according to the seventh embodiment. FIGS. 33, 34, 35, and 36 illustrate the image data indicating the positions of the corneal reflex centers 113C when the indicator 130 displayed at each of the positions PD1, PD2, PD3, PD4, and PD5 in the display screen 101S is shown to the test subject as described in the sixth embodiment.

Figure 33:
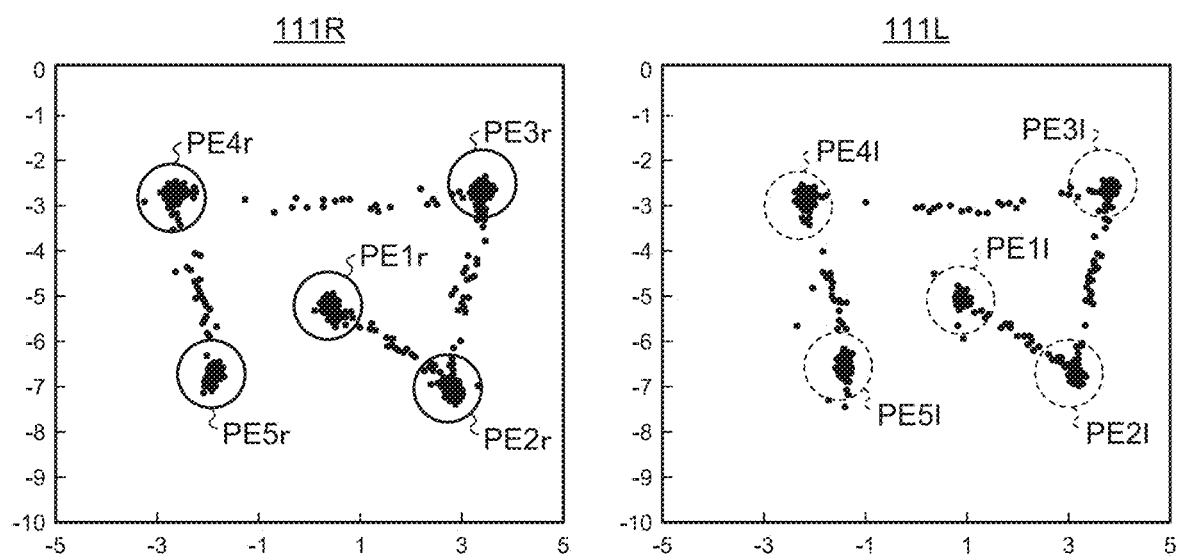
FIG. 33 is a diagram illustrating an example of the image data of the eyes of a test subject according to a seventh embodiment.

FIG. 33 illustrates the image data indicating the position of the corneal reflex center 113Cr of the right eye 111R and the position of the corneal reflex center 113Cl of the left eye 111L when the display screen 101S is shown to the test subject who does not have the tendency for strabismus. The position data of the corneal reflex centers 113C is obtained for 50 times in one second, for example.

When the test subject looks at the indicator 130 displayed at the position PD1 in the display screen 101S, a position PE1$r$ of the corneal reflex center 113Cr of the right eye 111R is decided based on the density of the corneal reflex center 113Cr. In an identical manner, when the test subject looks at the indicator 130 displayed at each of the positions PD2, PD3, PD4, and PD5 in the display screen 101S; positions PE2$r$, PE3$r$, PE4$r$, and PE5$r$, respectively, of the corneal reflex center 113Cr of the right eye 111R are decided based on the density of the corneal reflex center 113Cr.

When the test subject looks at the indicator 130 displayed at the position PD1 in the display screen 101S, a position PE11 of the corneal reflex center 113C1 of the left eye 111L is decided based on the density of the corneal reflex center 113C1. In an identical manner, when the test subject looks at the indicator 130 displayed at each of the positions PD2, PD3, PD4, and PD5 in the display screen 101S; positions PE21, PE31, PE41, and PE51, respectively, of the corneal reflex center 113C1 of the left eye 111L are decided based on the density of the corneal reflex center 113C1.

Figure 34:
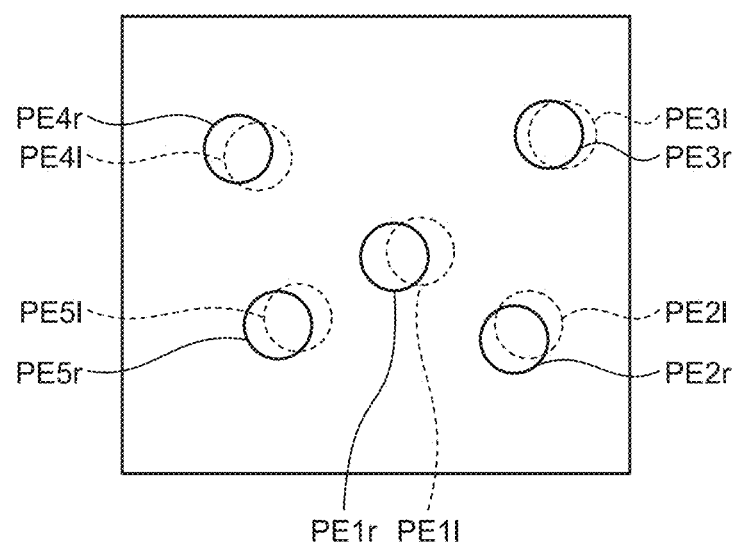
FIG. 34 is a diagram illustrating the example of the image data of the eyes of the test subject according to the seventh embodiment.

FIG. 34 illustrates the image data obtained by synthesizing the positions PE1r, PE2r, PE3r, PE4r, and PE5r regarding the right eye 111R with the positions PE11, PE21, PE31, PE41, and PE51 regarding the left eye 111L of the test subject who does not have the tendency for strabismus. FIG. 34 illustrates the image data obtained when the position of the pupil center 112Cr of the right eye 111R and the position of the pupil center 112C1 of the left eye 111L are set to be coincident in the X-Y plane.

With reference to FIG. 34, regarding the test subject who does not have the tendency for strabismus, the position PE1r is essentially coincident with the position PE11. In an identical manner, regarding the test subject who does not have the tendency for strabismus, the position PE2r is essentially coincident with the position PE21; the position PE3r is essentially coincident with the position PE31; the position PE4r is essentially coincident with the position PE41; and the position PE5r is essentially coincident with the position PE51.

Figure 35:
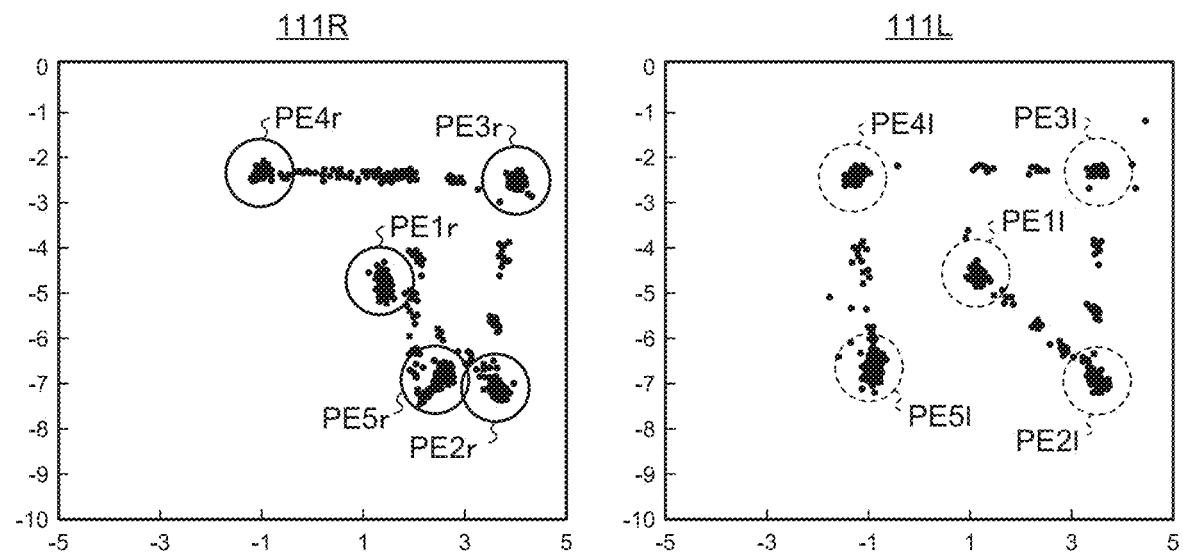
FIG. 35 is a diagram illustrating the example of the image data of the eyes of the test subject according to the seventh embodiment.
Figure 36:
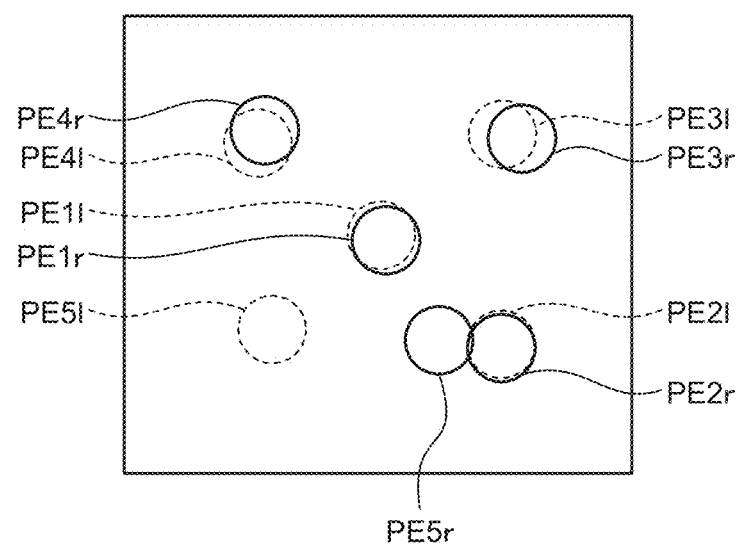
FIG. 36 is a diagram illustrating the example of the image data of the eyes of the test subject according to the seventh embodiment.

FIG. 35 illustrates the image data indicating the position of the corneal reflex center 113Cr of the right eye 111R and the position of the corneal reflex center 113C1 of the left eye 111L when the display screen 101S is shown to the test subject who has the tendency for strabismus. FIG. 36 illustrates the image data obtained by synthesizing the positions PE1r, PE2r, PE3r, PE4r, and PE5r regarding the right eye 111R with the positions PE11, PE21, PE31, PE41, and PE51 regarding the left eye 111L of the test subject who has the tendency for strabismus. As illustrated in FIG. 36, regarding the test subject who has the tendency for strabismus, for example, the positions PE5r and PE51 are not coincident with each other.

As explained above, the tendency for strabismus can be evaluated based on the image data obtained by synthesizing the positions PE1r, PE2r, PE3r, PE4r, and PE5r regarding the right eye 111R with the positions PE11, PE21, PE31, PE41, and PE51 regarding the left eye 111L.

Eighth Embodiment

Given below is the explanation of an eighth embodiment. In the following explanation, the constituent elements that are identical or equivalent to the embodiments described above are referred to by the same reference numerals, and their explanation is either simplified or omitted.

The eighth embodiment represents an application example of the sixth embodiment or the seventh embodiment. In the eighth embodiment, the explanation is given for an example in which a first-type vector Yd, which is directed from one indicator 130 toward the other indicator 130 in a pair of neighboring indicators 130 in the display screen 101S, is compared with a second-type vector Ye, which is directed from one corneal reflex 113 to the other corneal reflex 113 in the pair of neighboring corneal reflexes 113 formed when the concerned indicators 130 are viewed; and the degree of similarity between the first figure CA1 and the second figure CA2 is determined.

Figure 37:
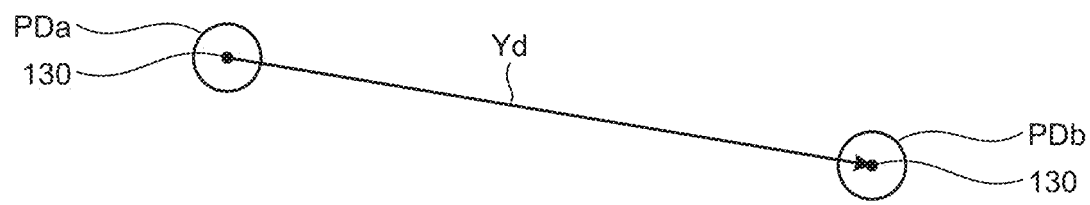
FIG. 37 is a schematic diagram for explaining an example of the strabismus examination method according to an eighth embodiment.
Figure 38:
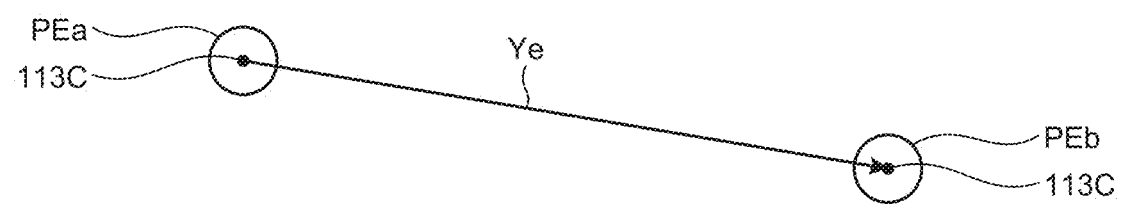
FIG. 38 is a schematic diagram for explaining the example of the strabismus examination method according to the eighth embodiment.
Figure 39:
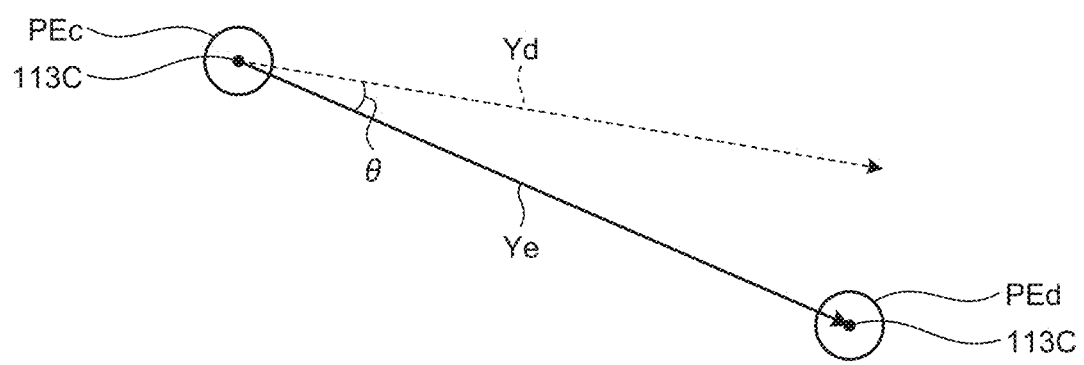
FIG. 39 is a schematic diagram for explaining the example of the strabismus examination method according to the eighth embodiment.

FIGS. 37, 38, and 39 are schematic diagrams for explaining an example of the strabismus examination method according to the eighth embodiment. FIG. 37 illustrates the first-type vector Yd that is directed from one indicator 130 to the other indicator 130 in a pair of neighboring indicators 130 in the display screen 101S. FIG. 38 illustrates the second-type vector Ye that is directed from one corneal reflex center 113C to the other corneal reflex center 113C in a pair of neighboring corneal reflex centers 113C formed when the test subject who does not have the tendency for strabismus looks at the indicators 130 illustrated in FIG. 37. FIG. 39 illustrates the second-type vector Ye that is directed from one corneal reflex center 113C to the other corneal reflex center 113C in a pair of neighboring corneal reflex centers 113C formed when the test subject who has the tendency for strabismus looks at the indicators 130 illustrated in FIG. 37.

With reference to FIG. 37, the indicator 130 is sequentially displayed at positions PDa and PDb in the display screen 101S. The indicator 130 displayed at the position PDa and the indicator 130 displayed at the position PDb are neighboring each other. The first-type vector Yd is assumed to be directed from the indicator 130 displayed at the position PDa to the indicator 130 displayed at the position PDb.

As illustrated in FIG. 38, when the test subject who does not have the tendency for strabismus looks at the indicator 130 displayed at the position PDa, the corneal reflex center 113C is formed at a position PEa. Similarly, when the test subject who does not have the tendency for strabismus looks at the indicator 130 displayed at the position PDb, the corneal reflex center 113C is formed at a position PEb. The corneal reflex center 113C formed at the position PEa and the corneal reflex center 113C formed at the position PEb are neighboring each other. The second-type vector Ye is assumed to be directed from the corneal reflex center 113C formed at the position PEa to the corneal reflex center 113C formed at the position PEb.

As illustrated in FIG. 38, regarding the test subject who does not have the tendency for strabismus, the second-type vector Ye is essentially parallel to the first-type vector Yd.

As illustrated in FIG. 39, when the test subject who has the tendency for strabismus looks at the indicator 130 displayed at the position PDa, the corneal reflex center 113C is formed at a position PEc. Similarly, when the test subject who has the tendency for strabismus looks at the indicator 130 displayed at the position PDb, the corneal reflex center 113C is formed at a position PEd. The corneal reflex center 113C formed at the position PEc and the corneal reflex center 113C formed at the position PEd are neighboring each other. The second-type vector Ye is assumed to be directed from the corneal reflex center 113C formed at the position PEc to the corneal reflex center 113C formed at the position PEd.

As illustrated in FIG. 39, regarding the test subject who has the tendency for strabismus, the second-type vector Ye is more likely to be nonparallel to the first-type vector Yd.

In this way, with reference to the direction of the first-type vector Yd, the direction of the second-type vector Ye regarding the test subject who does not have the tendency for strabismus is more likely to be different than the direction of the second-type vector Ye regarding the test subject who has the tendency for strabismus. Hence, by comparing the first-type vector Yd with the second-type vector Ye, the evaluating unit 218 can determine the degree of similarity between the first figure CA1 and the second figure CA2.

In the eighth embodiment, the evaluating unit 218 determines whether or not an angle θ formed between the first-type vector Yd and the second-type vector Ye is equal to or greater than a threshold value. If it is determined that the angle θ is equal to or greater than the threshold value, then the evaluating unit 218 determines that the test subject has the tendency for strabismus and outputs the evaluation data indicating that the test subject has the tendency for strabismus. On the other hand, if it is determined that the angle θ is not equal to or greater than the threshold value, then the evaluating unit 218 determines that the test subject does not have the tendency for strabismus and outputs the evaluation data indicating that the test subject does not have the tendency for strabismus.

Herein, the threshold value for the angle θ is derived either statistically or empirically based on the data obtained from a plurality of test subjects who have the tendency for strabismus, and is stored in the memory unit 220. For example, the threshold value for the angle θ is set in the range from equal to or greater than 15 [°] to equal to or smaller than 45 [°]. In the eighth embodiment, the threshold value for the angle θ is set to 20 [°].

As explained above, the visual performance of the test subject can be evaluated based on the first-type vector Yd and the second-type vector Ye. According to the eighth embodiment, it becomes possible to reduce the load of the arithmetic processing performed during strabismus examination.

Meanwhile, in the sixth, seventh, and eighth embodiments; the first figure CA1 need not have a square shape, and alternatively may have a rectangular shape, or a parallelogram shape, or a trapezoid shape. Moreover, the first figure CA1 need not be quadrilateral, and may alternatively be triangular, or polygonal having five or more sides, or may be circular, or may be elliptical.

INDUSTRIAL APPLICABILITY

The embodiments described above are suitable for examining the visual performance of the test subject.

According to an aspect of the present disclosure, even if there is variation in the relative position between the light source and the test subject, it becomes possible to hold down a decline in the examination accuracy of the visual performance.

What is claimed is:

1. A visual performance examination device, comprising:
a display control unit that displays an indicator at each of a plurality of positions on a display screen of a display device;
an image data obtaining unit that obtains image data of eyes of a test subject, which are irradiated with a detection light emitted from a light source;
a position calculating unit that, based on the image data, calculates a position data of corneal reflexes of the eyes when each of a plurality of indicators displayed at the positions in the display screen is shown; and
an evaluating unit that, based on relative positions of the indicators and relative positions of the corneal reflexes, outputs evaluation data about visual performance of the test subject, wherein the evaluating unit outputs the evaluation data based on a degree of similarity between a first figure that is defined according to the relative positions of the indicators and a second figure that is defined according to the relative positions of the corneal reflexes.

2. The visual performance examination device according to claim 1, wherein
the display control unit sequentially displays the indicator at each of the positions on the display screen, and
the evaluating unit compares a distance between neighboring corneal reflexes with a threshold value, and determines the degree of similarity between the first figure and the second figure.

3. The visual performance examination device according to claim 1, wherein:
the display control unit sequentially displays the indicator at each of the positions on the display screen; and
the evaluating unit compares a first-type vector, which is directed from one indicator towards another indicator in a pair of neighboring indicators on the display screen, with a second-type vector, which is directed from one corneal reflex to other corneal reflex in the pair of neighboring corneal reflexes, and outputs the evaluation data.

4. The visual performance examination device according to claim 1, further comprising:
an eye gaze detecting unit that detects, based on the image data, an eye gaze of the test subject.

5. A visual performance examination method, comprising:
displaying an indicator at each of a plurality of positions on a display screen of a display device;
obtaining image data of eyes of a test subject, which are irradiated with a detection light emitted from a light source;
calculating a position data of corneal reflexes of the eyes based on the image data when each of a plurality of indicators is shown; and
based on relative positions of the indicators and relative positions of the corneal reflexes, outputting evaluation data about visual performance of the test subject, wherein the evaluation data is outputted based on a degree of similarity between a first figure that is defined according to the relative positions of the indicators and a second figure that is defined according to the relative positions of the corneal reflexes.

6. A non-transitory computer readable recording medium storing therein a program that causes a computer to execute:
displaying an indicator at each of a plurality of positions on a display screen of a display device;
obtaining image data of eyes of a test subject, which are irradiated with a detection light emitted from a light source;
calculating a position data of corneal reflexes of the eyes based on the image data when each of a plurality of indicators is shown; and
based on relative positions of the indicators and relative positions of the corneal reflexes, outputting evaluation data about visual performance of the test subject, wherein the evaluation data is outputted based on a degree of similarity between a first figure that is defined according to the relative positions of the indicators and a second figure that is defined according to the relative positions of the corneal reflexes.

* * * * *